(12) United States Patent
Rosenberg

(10) Patent No.: US 8,624,077 B2
(45) Date of Patent: Jan. 7, 2014

(54) INTERFACE LAYER WOUND DRESSING

(75) Inventor: Lior Rosenberg, Omer (IL)

(73) Assignee: L.R.R.&D. Ltd., Omer (IL)

( * ) Notice: Subject to any disclaimer, the term of this patent is extended or adjusted under 35 U.S.C. 154(b) by 226 days.

(21) Appl. No.: 13/121,943

(22) PCT Filed: Oct. 1, 2009

(86) PCT No.: PCT/IL2009/000946
§ 371 (c)(1), (2), (4) Date: Jun. 6, 2011

(87) PCT Pub. No.: WO2010/038231
PCT Pub. Date: Apr. 8, 2010

(65) Prior Publication Data
US 2011/0275972 A1 Nov. 10, 2011

Related U.S. Application Data

(60) Provisional application No. 61/102,013, filed on Oct. 2, 2008.

(51) Int. Cl.
*A61F 13/00* (2006.01)

(52) U.S. Cl.
USPC .............................. 602/42; 602/43; 602/46

(58) Field of Classification Search
USPC ...................................... 602/41–54
See application file for complete search history.

(56) References Cited

U.S. PATENT DOCUMENTS

| | | | |
|---|---|---|---|
| 3,194,773 A | 7/1965 | Hostettler | |
| 3,383,351 A | 5/1968 | Stamberger | |
| 3,396,081 A | 8/1968 | Billek | |
| 3,454,505 A | 7/1969 | Cross | |
| 3,648,692 A | 3/1972 | Wheeler | |
| 3,927,669 A | 12/1975 | Glatt | |
| 3,975,567 A | 8/1976 | Lock | |
| 3,978,266 A | 8/1976 | Lock | |
| 3,993,576 A | 11/1976 | Barron | |
| 4,141,973 A | 2/1979 | Balazs | |
| 4,233,969 A | 11/1980 | Lock | |
| 4,303,676 A | 12/1981 | Balazs | |
| 4,385,133 A | 5/1983 | Alberino | |

(Continued)

FOREIGN PATENT DOCUMENTS

| JP | H07-80020 | 3/1995 |
|---|---|---|
| JP | 2003180812 | 7/2003 |

(Continued)

OTHER PUBLICATIONS

Cho et al., Hyaluronic acid and silver sulfadiazine-impregnated polyurethane foams for wound dressing application. J Mater Sci Mater Med. 2002; 13(9): 861-5.

(Continued)

*Primary Examiner* — Michael A. Brown
(74) *Attorney, Agent, or Firm* — Rodney J. Fuller; Booth Udall Fuller, PLC

(57) ABSTRACT

The invention relates to a wound dressing and methods of preparation and use thereof for promoting healing of a wound bed. In particular, the wound dressing is advantageous for application to a debrided wound bed. The wound dressing comprises an open conduit polymeric foam matrix, and a hydrophilic polymer which is disposed in dry form on the inner surfaces of the conduits within the matrix.

25 Claims, 7 Drawing Sheets

(56) References Cited

U.S. PATENT DOCUMENTS

| | | | | |
|---|---|---|---|---|
| 4,517,295 | A | 5/1985 | Bracke | |
| 4,550,126 | A | 10/1985 | Lorenz | |
| 4,570,629 | A * | 2/1986 | Widra | 604/304 |
| 4,582,865 | A | 4/1986 | Balazs | |
| 4,655,210 | A | 4/1987 | Edenbaum | |
| 4,670,477 | A | 6/1987 | Kelly | |
| 4,713,448 | A | 12/1987 | Balazs | |
| 4,733,659 | A | 3/1988 | Edenbaum | |
| 4,736,024 | A | 4/1988 | Della Valle | |
| 4,780,414 | A | 10/1988 | Nimrod | |
| 4,784,990 | A | 11/1988 | Nimrod | |
| 4,808,576 | A | 2/1989 | Schultz | |
| 4,863,976 | A | 9/1989 | Nichols | |
| 4,946,780 | A | 8/1990 | Hashimoto | |
| 4,950,694 | A | 8/1990 | Hager | |
| 5,015,577 | A | 5/1991 | Weigel | |
| 5,128,326 | A | 7/1992 | Balazs | |
| 5,447,505 | A * | 9/1995 | Valentine et al. | 604/304 |
| 5,616,568 | A | 4/1997 | Pouyani | |
| 5,644,049 | A | 7/1997 | Giusti | |
| 5,782,787 | A | 7/1998 | Webster | |
| 5,844,013 | A | 12/1998 | Kenndoff | |
| 5,874,417 | A | 2/1999 | Prestwich | |
| 6,552,244 | B1 | 4/2003 | Jacques | |
| 6,596,293 | B1 | 7/2003 | Bootman | |
| 6,610,666 | B1 | 8/2003 | Akerblom | |
| 6,630,457 | B1 | 10/2003 | Aeschlimann | |
| 6,656,974 | B1 | 12/2003 | Renn | |
| 6,803,495 | B2 | 10/2004 | Simpson | |
| 6,855,860 | B2 * | 2/2005 | Ruszczak et al. | 602/48 |
| 7,041,868 | B2 | 5/2006 | Greene | |
| 7,112,417 | B2 | 9/2006 | Vyakarnam | |
| 2007/0185426 | A1 | 8/2007 | Ambrosio | |
| 2007/0254974 | A1 | 11/2007 | Mager | |
| 2007/0299383 | A1 * | 12/2007 | Murphy et al. | 602/46 |
| 2008/0146983 | A1 * | 6/2008 | Park et al. | 602/46 |
| 2010/0298791 | A1 * | 11/2010 | Jones et al. | 604/319 |

FOREIGN PATENT DOCUMENTS

| | | |
|---|---|---|
| JP | 2008/149103 | 7/2008 |
| WO | 98/53850 | 12/1998 |
| WO | 00/01733 | 1/2000 |
| WO | 2004/039421 | 5/2004 |
| WO | 2005/052043 | 6/2005 |
| WO | 2006/006167 | 1/2006 |

OTHER PUBLICATIONS

Davidson et al., Hyaluronate derivatives and their application to wound healing: preliminary observations. Clin Mater 1991; 8(1-2): 171-7.

Rosenberg et al., Safety and efficacy of a proteolytic enzyme for enzymatic burn debridement: a preliminary report. Burns 2004; 30(8): 843-50.

Office Action for Japanese Patent Application No. 2011-529677 dated Oct. 1, 2013.

* cited by examiner

Fig. 4a
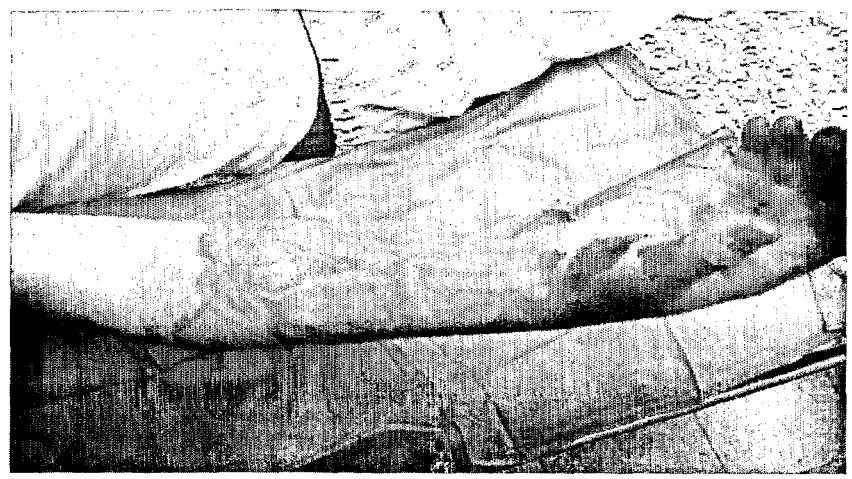
Fig. 4b
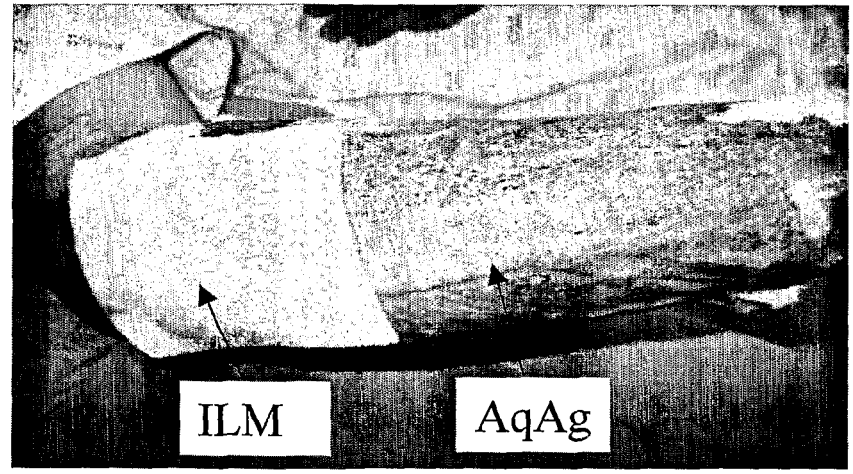
Fig. 4c
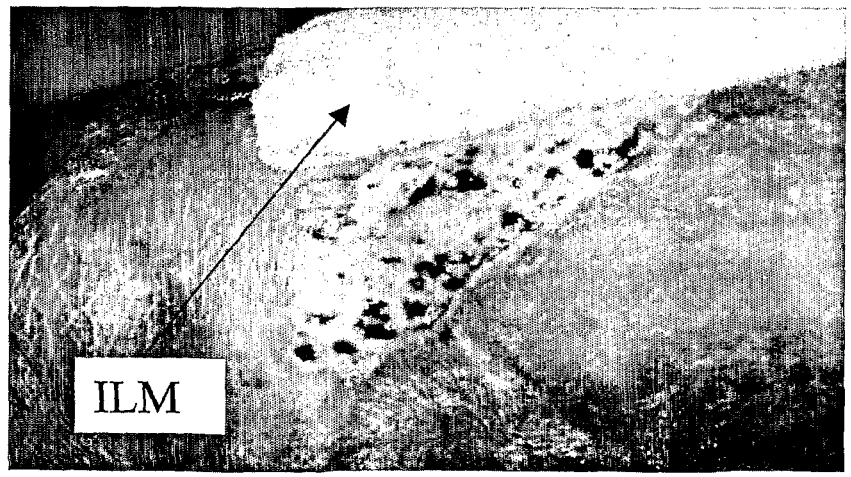
Figure 4

Figure 4, continued

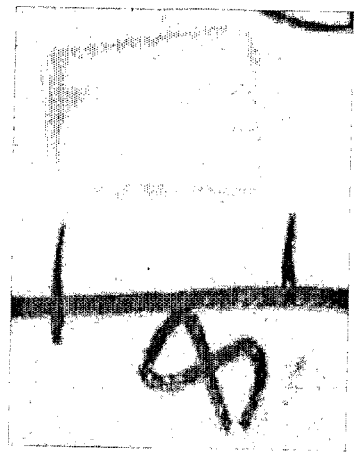 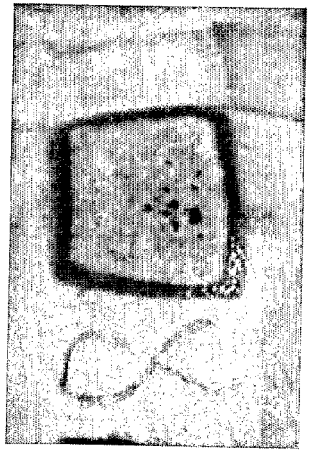 
Fig. 5a      Fig. 5b      Fig. 5c
 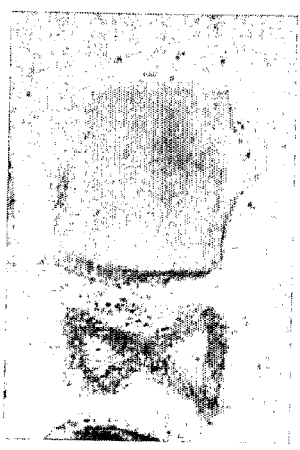 
Fig. 5d      Fig. 5e      Fig. 5f
Figure 5

  
Fig. 5g　　　Fig. 5h　　　Fig. 5i
Fig. 5j
Figure 5, continued

INTERFACE LAYER WOUND DRESSING

RELATED APPLICATION DATA

This application is the U.S. National Stage of PCT/IL2009/000946, filed Oct. 1, 2009, which claims the benefit of U.S. Provisional Patent Application No. 61/102,013, filed Oct. 2, 2008, the contents of each of which are herein incorporated by reference for all purposes.

FIELD OF THE INVENTION

The invention relates to a wound dressing and use thereof particularly for treating a debrided wound bed. The dressing comprises an open conduit polymeric foam matrix, and a hydrophilic polysaccharide which is disposed in dry form on the inner surfaces of the conduits within the matrix.

BACKGROUND OF THE INVENTION

Skin wounds disrupt the continuity of the protective tissue interface between the inner organs of the human body and the external environment. Causes of skin wounds include burns, resulting from exposure to thermal extremes, radiation (UV or ionizing) or chemicals; mechanical injury, and pathologic conditions associated with necrotic complications, in particular diabetes, high blood pressure and vascular diseases.

Wound bed preparation (WBP) refers to a medical intervention activity aimed at any or all of: cleaning the wound bed of any foreign material and/or dead tissue (such as eschar in the case of burned skin); increasing the amount of granulation tissue in chronic and recalcitrant wounds; reducing the number of abnormal or senescent cells within the wound or at the wound edge; decreasing exudates and edema; and decreasing bacterial burden, so as to initiate and promote the wound healing process. The technology selected for WBP depends on the wound etiology and in turn, influences the nature and subsequent behavior of the wound bed. Debridement is usually an essential component of wound bed preparation.

Surgical debridement involves excision of clinically diagnosed dead tissues, and is terminated at a point when the surgeon judges that the wound bed is clean, usually on the basis of the bleeding pattern. This method is traumatic and non-selectively sacrifices large amounts of uninjured tissue, but is quick and effective. The surgically debrided wound bed is characterized by a raw surface with sharply transected cutaneous components, mainly dermal collagen matrix, skin appendages (hair roots, sweat and sebaceous glands) and blood vessels. The transected dermal matrix is bleeding, flat and smooth. If sufficient dermis remains with epithelial components from the appendages, this bed may heal by epithelialization upon provision of proper conditions. Near or full thickness defects may be repaired by autografting under stabilizing and protective dressing. This scenario is typical for acute and burn wounds.

Conventional (or "conservative") non-surgical debridement involves application of chemical and/or other topical preparations, soakings and repeated dressings over a long period of time i.e. up to several weeks. Accordingly, this technique is considerably slower and less efficient than surgical debridement. The resultant wound bed is usually a mixture of exposed tissues, granulating tissue, fibrinous deposits with possible residues of eschar, pus and bacterial aggregates. Healing may require additional surgery and autografting. This condition typifies chronic, recalcitrant and slow healing acute wounds.

A more recent debridement technique, in particular for burn wounds, is rapid enzymatic debridement using mixtures of proteolytic enzymes. Particularly effective are proteolytic enzymes extracted from the stem of the pineapple plant, as disclosed by the inventor of the present invention, for example in WO 98/053850 and WO 2006/0006167, and as provided in the product marketed under the trade name Debrase®.

This technique is reported to selectively remove dead tissue within four hours of application, and leave healthy tissue substantially intact. Accordingly, rapid enzymatic debridement may also be referred to as "selective enzymatic debridement" when only dead tissue is eliminated. The resultant wound bed is characterized by a raw surface dermal matrix that has a "furred" appearance, in contrast to surgically debrided and sharply transected tissue. Blood vessels and skin appendages in the wound bed may be partially occluded, and significant portions of dermis are preserved with epithelial components from the appendages. This type of wound bed may heal by epithelialization upon provision of proper conditions. Near or full thickness defects may be repaired by autografting under stabilizing and protective dressing.

The raw surface remaining after rapid enzymatic debridement comprises the upper layer of remaining healthy tissue, and may be defined as the "interface layer". All viable components in the interface layer, such as epithelial elements and dermal remnants, form the basis for spontaneous epithelialization and healing. The interface layer has biological and physiological characteristics which differ from that of the surgically or conventional non-surgically debrided beds. For example, the surgically debrided bed consists of transected tissue and its structures and requires protection, mainly against desiccation. The conventional non-surgically debrided bed contains smaller or larger quantities of granulation tissue, which requires different care than the raw surface, particularly upon formation of bacterial biofilm. The interface layer resulting from selective enzymatic debridement needs a specific, dynamic dressing that should comply to its changing needs in order to promote the healing process. The prior art does not provide any such means for providing a dynamic and adjustable microenvironment in the interface layer.

The prior art discloses various synthetic polymer-biopolymer composite materials, including coverings and dressings for burns and other wounds. Many such materials include open cell polymeric foams i.e. foams characterized by interconnecting pores or conduits which open to the outer surfaces. Such foams often form a part of a multi-layered structure; in some cases a separate layer is formed from a biopolymer such as hyaluronic acid. Other disclosures relate to co-polymers, cross-linked forms and covalently linked combinations of polyurethanes and hyaluronic acid.

U.S. Pat. No. 7,112,417 discloses a composite for tissue engineering and other tissue applications, comprising a biocompatible filamentous first layer and a biocompatible foam second layer, wherein the foam preferably has a gradient structure, is bioabsorbable and is inter alia an aliphatic polyester. According to the disclosure, the interconnecting pores of the foam are in the size range from about 10 µm to about 200 µm or greater, and may be co-lyophilized, coated or filled with pharmaceutically active compounds or biopolymers inter alia hyaluronic acid.

U.S. Pat. No. 6,552,244 discloses a multi-layered wound dressing which comprises: (a) an absorbent layer inter alia a fibrous layer comprising gel-forming fibres inter alia hyaluronic acid, having a water absorbency of at least 10 µg with a low lateral wicking rate; (b) a transmission layer inter alia a polyurethane foam, having a high moisture vapor transmission rate overlying the side of said absorbent layer furthest from the wound during use; and, (c) a spreading layer having high lateral wicking rate disposed between the absorbent and transmission layer.

U.S. Pat. No. 6,855,860 discloses a non-occlusive composite wound dressing comprising a natural polymer wound-healing layer comprising isolated polymer fibers, and a synthetic polymer foam layer having at least one pore-containing surface contacting said natural layer and physically adhered to said natural layer. According to the disclosure, the synthetic polymer may be an open-pore polyurethane foam, the natural polymer may be a polysaccharide, and the natural polymer layer may incorporate a wound healing agent inter alia glycosaminoglycans.

U.S. Pat. No. 7,041,868 discloses a wound dressing comprising a first layer located adjacent to the wound comprising a fibrous non-woven bioabsorbable material, having pores in the size range 50-400 microns, adapted for serving as a scaffold for cell attachment and proliferation; and a second layer which is in contact with the first layer comprising an absorbent gel forming material and adapted for serving as a barrier to cell adhesion and penetration. According to the disclosure, the first layer can be formed from inter alia cross-linked hyaluronic acid, or can include hyaluronic acid as a fiber coating, or it can be a foam, and the second layer may be inter alia a foam or hydrogel or any structure having pore size less than about 10 microns in the hydrated state.

U.S. Pat. No. 6,596,293 discloses a polymeric delivery device for controlled release of a bioactive agent, the device formed by treating a biopolymer with a cross-linking agent whereby the cross-linking agent is simultaneously polymerized and formed into cross-linking moieties with the biopolymers, According to the disclosure, the preferred cross-linking agents are polyisocyanate-terminated polyurethane or polyurethane urea pre-polymers, which upon use of water as solvent results in a foam material. It is further disclosed that suitable biopolymers include glycosaminoglycan from animal tissue.

U.S. Pat. No. 6,656,974 discloses a foam material for wound dressings, comprising a solid cross-linked form of an anionic polymer, which is preferably an alignate, and may further comprise hyaluronic acid. According to the disclosure, the foam may incorporate inter alia a hydrophilic polymer or a wound healing agent.

U.S. Pat. No. 5,644,049 discloses a biomaterial comprising a non-chemically crosslinked interpenetrating polymer network comprising a first component selected from a hyaluronic acid ester and a hyaluronic acid salt, and a second component which is a synthetic chemical polymer. This patent discloses inter alia formation of transparent homogeneous films by amalgamation of various hyaluronic acid derivatives and polyurethanes.

U.S. Patent Application Publication No. 2007/0185426 discloses a delivery system for applying reduced pressure tissue treatment to a tissue site inter alia a burn wound, comprising a multi-layer apparatus having a tissue contact layer which includes a scaffold; a release layer and a manifold layer. According to the disclosure, the invention is a biocompatible wound dressing which includes a foam pad, preferably comprising highly reticulated open-cell polyurethane foam, and the tissue contact layer may include inter alia hyaluronic acid. The pore size of the scaffold may be between 50 and 500 microns.

PCT publication No. WO 2005/052043 discloses a flexible polyurethane foam for cosmetic puffs containing 0.001 to 2% by mass hyaluronic acid, which is formed by a process comprising mixing organic polyisocyanate, polyol, catalyst, foam stabilizer, aqueous hyaluronic acid solution and an inert gas, followed by foaming and curing.

PCT publication No. WO 2004/039421 discloses a polyurethane foam dressing for a wound filler, which includes a hydrophilic foam containing a plurality of open cells with a diameter of 50 to 400 microns and a plurality of pores with a diameter of 10 to 80 microns. According to the disclosure, the foam is produced by mixing and agitating 40 to 75 wt % pre-polymer, 15 to 45 wt % foaming agent, 5 to 35 wt % crosslinking agent, 0.5 to 15 wt % additive containing a surfactant, a moisturizing agent, and a pigment, injecting the resulting mixture into a mold, and foaming the mixture while it is injected into the mold. Further disclosed is that the additive and/or the moisturizing agent may be inter alia hyaluronic acid.

Cho et al discloses preparation and relative efficacy of polyurethane foam wound dressings including various additives inter alia hyaluronic acid, alone or hyaluronic acid in combination with silver sulfadiazine. According to the disclosure, impregnated polyurethane foams are formed by incorporating the additives into the polyurethane foaming reaction and have open cells of 50 to 200 microns and density of 0.234 to 0.26 g/cm$^3$ (Cho et al (2002) J Mater Sci Mater Med. 13(9):861-5).

Davidson et al disclose use of hyaluronic acid and hyaluronic acid ethyl ester formulations in a sodium alginate vehicle under an occlusive, polyurethane dressing for wound healing in experimental animal systems (Davidson et al (1991) Clin Mater 8(1-2):171-7).

Wound dressings incorporating hydrophilic, water-absorptive polyurethane materials are disclosed for example, in U.S. Pat. Nos. 6,803,495; 5,844,013; 5,782,787; 4,733,659; 4,655,210; 4,550,126; 4,233,969; 3,978,266; 3,927,669, and 3,648,692 and in Patent Application Publication No. 2007/0254974.

Numerous wound dressings are commercially available, including for example, foam-based products such as PolyMem™ and Biatain™; hyaluronan-based products such as Hyalomatrix™, Jaloskin™ and collagen-based products such as Fibracol™ and Integra™. None of the prior art products are designed for use in wound beds following rapid enzymatic debridement, nor do the prior art products enable delivery of different pharmaceutical agents according to changing conditions and progressive stages of healing in the interface layer, without removing the dressing layer and disruption of the healing wound.

There remains an unmet need for a wound dressing that facilitates delivery, exchange or withdrawal of different pharmaceutical agents or substances according to changing conditions and progressive stages of healing in an interface layer microenvironment, without removal of the dressing layer and disruption of the healing wound. There is also an unmet need for a wound dressing that is appropriate for use in wound beds following debridement by various means, including rapid enzymatic debridement.

SUMMARY OF THE INVENTION

The present invention provides a wound dressing for application onto a wound bed following debridement, and methods of use thereof to create an interface layer microenvironment (ILM) conducive to wound healing. The inventor arrived at the present invention in the course of studying clinical management of enzymatically debrided wound beds, for which appropriate dynamic dressings were not previously available. In particular, the relatively new approach of wound bed preparation utilizing rapid and selective enzymatic debridement introduced a new type of clinical situation that could not be effectively addressed by prior art wound dressings.

It has surprisingly been found that the invention is particularly effective for promoting healing of wounds following selective enzymatic debridement using enzyme preparations derived from the pineapple product termed bromelain. One such product is currently in an advanced phase of clinical trials (Rosenberg et al. Burns. 2004 Dec; 30(8):843-50). The invention is also effective for use on wound beds treated by other means such as surgical debridement and "conservative" non-surgical debridement.

The wound dressing of the invention comprises an open conduit polymer foam, and a hydrophilic polysaccharide disposed in dry form on the inner surfaces of the conduits within the foam. The conduits form an interconnecting network of channels within the foam, and are "open" since they have openings at the outer surfaces of the foam. The conduits are of sufficiently large diameter so as to permit passage of fluids, even when the hydrophilic polysaccharide within the matrix is in a hydrated swollen state.

It is to be explicitly understood that the invention does not encompass a dressing in which the polymer foam and the hydrophilic polysaccharide are provided in separate distinct layers, such as in a multi-layer wound dressing. Furthermore, is to be understood that the hydrophilic polysaccharide and the polymer foam are not in the form of any of: a co-polymer, a cross-linked conjugate or a covalently linked conjugate.

Rather, in the present invention, the hydrophilic polysaccharide is added to a pre-formed foam, and is present in dry form as a dispersal, deposit or coating on the inner surfaces of the conduits within the foam. Optionally, the hydrophilic polysaccharide may additionally be provided on at least one of the outer surfaces of the foam, preferably the outer surface of the foam which faces or is intended to directly contact the wound surface.

Without wishing to be bound by any particular theory or mechanism of action, the matrix wound dressing of the invention provides an adherent physical framework for healing tissue within a wound bed, and provides a means of delivering pharmaceutical agents without disruption of the healing tissue. Furthermore, the hydrophilic polysaccharide within the conduits absorbs exudates and serum from the wound thus forming a hydrated gel which provides a moist medium necessary for the healing process. While the dressing adheres to the healing surface by the interaction of the large conduit openings and the healing tissue, it substantially avoids the undesirable growth of granulation tissue or epithelium into the dressing. The dressing is preferably not biodegradable, since its degradation may stimulate inflammatory processes in the healing tissues, and other unfavorable conditions.

The wound dressing of the present invention is advantageous over previously known dressings since it enables modulating the conditions at the wound surface by delivery of different pharmaceutical agents according to changing conditions and/or progressive healing stages in the wound bed, without the need for removing the dressing. Its use does not require conventional adhesives which can interfere with the healing process and cause discomfort, since the large conduit foam adheres to the wound bed without excessive stickiness. It further controls infection, pain, moisture content and allows early mobilization and discharge; and it enables tissue preservation, epithelialization enhancement, and fibroblastic activity modulation. The invention may be applied to suboptimally debrided wound beds without extensive cleaning of the site, and it is compatible with debrided wound beds prepared by all currently employed means i.e. surgical, chemical, enzymatic. Additionally it is compatible with surfaces of implanted skin grafts, is easy to use, cost effective, readily available, has a long shelf life and uses a synthetic matrix.

In a first aspect, the present invention provides a wound dressing, in the form of a dry flat sheet of a synthetic polymer foam matrix having two opposed external surfaces, wherein a first external surface is configured to face the wound bed and a second external surface is exposed to the external environment, the matrix comprising an open conduit polymer foam and at least one gel-forming hydrophilic polysaccharide, wherein the polysaccharide is disposed in dry form on the inner surfaces of the open conduits within the foam.

In a particular embodiment, the polysaccharide is further disposed in dry form on at least one of the opposing external surfaces of the foam. In a particular embodiment, the polysaccharide is disposed in dry form on the external surface of the foam configured to face the wound bed. In a particular embodiment, the polysaccharide is disposed in dry form on both of the opposing external surfaces of the foam.

As used herein, the term "opposing external surfaces of the foam" refers to a first external surface of the foam configured to face the wound bed, and a second opposing external surface of the foam which is exposed to the environment.

In a currently preferred embodiment, the open conduit polymer foam comprises an open conduit polyurethane foam, and the hydrophilic polysaccharide comprises hyaluronic acid, or a pharmaceutically acceptable salt or derivative thereof.

In a particular embodiment, the polyurethane is selected from the group consisting of a polyester polyurethane, a polyether polyurethane and a cross-linked polyurethane. In another embodiment, the open conduit polymer foam comprises a material selected from the group consisting of: a polyolefin, a polyvinylchloride, polyvinylfluoride, a poly(vinylimidazole), a polyacrylate, a ethylene-vinyl acetate copolymer, a polystyrene and a polyethylene oxide. In a particular embodiment, the open conduit polymer foam is substantially non-biodegradable.

In a particular embodiment, the diameter of the conduits within the polymer foam is at least 300 μm. In a particular embodiment, the diameter of the conduits is between about 300 μm and about 5000 μm. In a particular embodiment, the diameter of the conduits is between about 300 μm and about 1000 μm. In a particular embodiment, the diameter of the conduits is about 500 μm. In a particular embodiment, the diameter of the conduits is between about 1000 μm and about 4000 μm. In a particular embodiment, the diameter of the conduits is between about 1000 μm and about 3000 μm. In a particular embodiment, the diameter of the conduits is greater than 5000 μm. Each possibility is a separate embodiment of the invention.

In a particular embodiment, the thickness of the dry flat sheet of the synthetic polymer foam matrix is in the range of about 2 to about 12 mm. In a particular embodiment, the thickness is about 4 to about 8 mm. As used herein, the thickness refers to the dimension of the matrix between the opposing external surfaces of the foam, measured prior to hydration.

In a particular embodiment, the polymer foam matrix has an absorption of at least 50% on a weight per weight (w/w) basis. In a particular embodiment, the absorption of the polymer foam matrix is greater than 100% (w/w).

In a particular embodiment, at least 75% of the conduits within the polymer foam are substantially continuous between the opposing external surfaces of the foam. In a particular embodiment, substantially 100% of the conduits within the polymer foam are substantially continuous between the opposing external surfaces of the foam.

In a particular embodiment, the polymer foam has from about 100 to about 1000 conduit openings per cm$^2$. In a particular embodiment, the polymer foam matrix has about 200 to about 500 conduit openings per cm$^2$. In a particular embodiment, the polymer foam matrix has about 300 conduit openings per cm$^2$. As used herein, the number of conduits openings refers to the number of conduit openings per unit surface area on an external surface of the foam, or a mean thereof.

In a particular embodiment, the polymer foam has a density between about 0.1 and about 0.4 g/cm$^3$. In a particular embodiment, the polymer foam has a density between about 0.1 and about 0.2 g/cm$^3$. In a particular embodiment, the polymer foam has a density between about 0.1 and about 0.15 g/cm$^3$. In a particular embodiment, the polymer foam matrix has an air transmission rate of between about 30 and about 90 liter/min. In a particular embodiment, the air transmission rate is about 60 liter/min. As used herein, the air transmission rate refers to that rate of air transfer across a 100 mm thickness of material having a surface area of 100 mm$^2$ under application of 5 atmospheric pressures.

In a particular embodiment, the polysaccharide is selected from the group consisting of: hyaluronic acid; a sulfated glycosaminoglycan; chitosan; alginate; hydroxyethyl cellulose; carboxymethyl cellulose; a cellulose derivative; pectin; gum arabic, starch, pharmaceutically acceptable salts thereof and combinations thereof.

In a currently preferred embodiment, the polysaccharide is hyaluronic acid or a pharmaceutically acceptable salt or derivative thereof. In a particular embodiment, the hyaluronic acid is cross-linked. In a particular embodiment, the hyaluronic acid is non-cross-linked.

In a particular embodiment, the hydrophilic polysaccharide is present in the wound dressing in an amount of from about 0.001 gram to about 1.0 gram per cm$^3$ of polymer foam. In particular embodiments, the hydrophilic polysaccharide is present in an amount of from about 0.001 gram to about 0.01 gram per cm$^3$ of polymer foam; or from about 0.01 gram to about 0.1 gram per cm$^3$ of polymer foam; or from about 0.1 gram to about 1.0 gram per cm$^3$ of polymer foam.

In a particular embodiment, the open conduit polymer foam comprises open conduit polyurethane, and the hydrophilic polysaccharide comprises hyaluronic acid, or a pharmaceutically acceptable salt or derivative thereof, wherein the diameter of the conduits within the polyurethane foam is between about 300 μm and about 5000 μm.

In a particular embodiment, the wound dressing comprises open conduit polyurethane foam and hyaluronic acid or a pharmaceutically acceptable salt or derivative thereof, wherein the diameter of the conduits within the polyurethane foam is between about 300 μm and about 1000 μm, wherein said hyaluronic acid or pharmaceutically acceptable salt or derivative thereof is present in an amount from about 0.001 gram to about 0.01 gram per cm$^3$ of polyurethane foam, and wherein the hyaluronic acid is disposed in dry form on the inner surfaces of the open conduits within the polyurethane foam.

In a particular embodiment, the hyaluronic acid is further disposed in dry form on one external surface of the polyurethane foam. In a particular embodiment, the hyaluronic acid is further disposed in dry form on the external surface of the polyurethane foam configured to face the wound bed. In a particular embodiment, the hyaluronic acid is further disposed in dry form on both opposing external surfaces of the polyurethane foam.

In a particular embodiment, the hyaluronic acid is present in an amount of from about 0.001 gram to about 0.1 gram per cm$^3$ of polyurethane foam. In a particular embodiment, the hyaluronic acid is present in an amount of from about 0.001 gram to about 0.01 gram per cm$^3$ of polyurethane foam. In particular embodiments, the hyaluronic acid is present in an amount of about 0.001; 0.002; 0.003; 0.004; 0.005; 0.006; 0.007; 0.008; 0.009, or 0.01 gram per cm$^3$ of polyurethane foam. In a particular embodiment, the hyaluronic acid is present in an amount of about 0.005 gram per cm$^3$ of polyurethane foam. In a particular embodiment, the diameter of the conduits within the polyurethane foam is about 500 μm. In a particular embodiment, the polyurethane foam has from about 200 to about 500 conduit openings per cm$^2$ of surface area, for example about 300 conduits per cm$^2$.

In a particular embodiment, the wound dressing further comprises a pharmaceutical agent selected from the group consisting of: a corticosteroid, a growth factor, a bacteriocidal agent, an antibiotic, an additional polysaccharide, and a plant extract. In a particular embodiment, the plant extract is derived from sea buckthorn (*Hippophae rhamnoides*). In a particular embodiment, the pharmaceutical agent is formulated with a pharmaceutically acceptable hydrophobic excipient. In a particular embodiment, the hydrophobic excipient is in particulate form. In a particular embodiment, the excipient is selected from the group consisting of: an oil, a micelle and a wax. In a particular embodiment, the pharmaceutical agent is disposed upon the external surface of the foam matrix which is exposed to the external environment and does not directly contact the wound bed. In a particular embodiment, the pharmaceutical agent is in a form selected from the group consisting of a solution, an oil, a foam, a gel, a cream and an ointment.

In a particular embodiment, the wound dressing is provided in sterile form within a packaging material. In a particular embodiment, the wound dressing is provided in unit format within a packaging material. In a particular embodiment, the unit format is a single unit or a multi-unit format. In a particular embodiment, the packaging material is a vacuum package. In a particular embodiment, the wound dressing is not a multi-layer dressing. In a particular embodiment, the wound dressing is substantially devoid of an adhesive material. In a particular embodiment, the wound dressing is a single layer dressing comprising polyurethane foam and hyaluronic acid.

In a particular embodiment, there is provided a method of producing the wound dressing of the invention, the method comprising: (i) applying the hydrophilic polysaccharide in the form of a solution or gel to at least one external surface of the polymer foam so as to cover said external surface; and (ii) subjecting the foam obtained in (i) to drying under vacuum. In a particular embodiment, the drying under vacuum comprises vacuum desiccation or lyophilization.

In a particular embodiment, the process further comprises (iii) impregnating the hydrophilic polysaccharide applied in (i) into the open conduits within the polymer foam, wherein (iii) is carried out prior to (ii). In a particular embodiment (iii) comprises an operation selected from the group consisting of centrifugation, application of negative pressure, application of positive pressure and application of vacuum.

In a particular embodiment, the amount of the hydrophilic polysaccharide applied to the external surface of the polymer foam in (i) is from about 0.1 to about 20.0 milligram (mg) per cm$^2$ of said external surface of the polymer foam. In a particular embodiment, the amount of the hydrophilic polysaccharide applied is from about 1.0 to about 10.0 mg per cm$^2$ of said external surface of the polymer foam.

In a particular embodiment, the method comprises: (i) applying hyaluronic acid or a pharmaceutically acceptable salt or derivative thereof in the form of a solution to at least one external surface of an open conduit polyurethane foam so as to cover said external surface; and (ii) subjecting the foam obtained in (i) to drying under vacuum. In a particular embodiment, the drying under vacuum comprises vacuum desiccation or lyophilization. In a particular embodiment, the method further comprises: (iii) subjecting the foam obtained in (i) to an operation selected from centrifugation and application of vacuum, wherein (iii) is carried out prior to (ii). In a particular embodiment, the amount of hyaluronic acid applied to the external surface of the polyurethane foam in (i) is from about 1.0 to about 10.0 mg per cm$^2$ of said external surface of the polyurethane foam.

In another aspect, the invention provides a method for promoting healing of a debrided wound bed in a subject in need thereof, the method comprising the step of applying over a debrided wound bed a wound dressing, wherein the wound dressing comprises an open conduit polymer foam and at least one gel-forming hydrophilic polysaccharide, wherein the hydrophilic polysaccharide is disposed in dry form on the exposed surfaces of the foam; thereby promoting healing of the debrided wound bed in the subject.

In a particular embodiment, the wound dressing comprises an open conduit polyurethane foam and hyaluronic acid or a pharmaceutically acceptable salt or derivative thereof, wherein the hyaluronic acid is disposed in dry form on the inner surfaces of the conduits within the polyurethane foam, and wherein the diameter of the conduits within the polyurethane foam is between about 300 μm and about 5000 μm. In a particular embodiment, the hyaluronic acid is present in an amount of from about 0.001 gram to about 0.01 gram per cm$^3$ of polyurethane foam.

In a particular embodiment, the hyaluronic acid is further disposed in dry form on one external surface of the polyurethane foam. In a particular embodiment, the hyaluronic acid is further disposed in dry form on the external surface of the polyurethane foam configured to face the wound bed. In a particular embodiment, the hyaluronic acid is further disposed in dry form on both opposing external surfaces of the polyurethane foam.

In a particular embodiment, the hyaluronic acid is cross-linked. In a particular embodiment, the hyaluronic acid is non-cross-linked. Other embodiments of the wound dressing are as hereinbefore described.

In a particular embodiment, the method is carried out on an enzymatically debrided wound bed. In a particular embodiment, the method is carried out following an enzymatic debridement procedure. In a particular embodiment, the enzymatic debridement comprises application of an enzyme selected from the group consisting of bromelain derivatives, debridase, collagenase, papain derivatives, streptokinase, sutilains, fibrinolysin, deoxyribonuclease, krill derivatives, trypsin and combinations thereof. In a particular embodiment, the method is carried out on a surgically debrided wound bed. In a particular embodiment, the method is carried out on a non-surgically conventionally debrided wound bed. In a particular embodiment, method is carried out on a wound bed originating from a wound selected from the group consisting of a chronic wound and an acute wound. In a particular embodiment, the chronic wound is selected from the group consisting of a venous/arterial insufficiency leg ulcer, a pressure ulcer and a diabetic foot ulcer. In a particular embodiment, the acute wound is selected from the group consisting of a burn, an amputation wound, an acute trauma, a skin graft donor site, a bite wound, a frostbite wound, a dermabrasion, and a surgical wound. In a particular embodiment, the burn is a full-thickness burn or a partial-thickness burn.

In a particular embodiment, the step of applying the wound dressing is carried out in the absence of an adhesive material.

In a particular embodiment, the wound dressing is maintained over the wound bed for a period of at least one week. In a particular embodiment, the wound dressing is maintained over the wound bed for a period of up to 2 weeks. In a particular embodiment, the wound dressing is maintained over the wound bed for a period of up to 4 weeks. In a particular embodiment, the wound dressing is maintained over the wound bed until epithelialization is completed.

In a particular embodiment, the method further comprises a step of applying a pharmaceutical agent to the external surface of the foam matrix which does not face the wound bed. In a particular embodiment, the pharmaceutical agent is in a form selected from the group consisting of a solution, an oil, a foam, a gel, a cream and an ointment. In a particular embodiment, the pharmaceutical agent is selected from the group consisting of: an additional polysaccharide, a corticosteroid, a growth factor, a bacteriocidal agent, an antibiotic, and a plant extract. In a particular embodiment, the pharmaceutical agent is a corticosteroid. In a particular embodiment, the plant extract is derived from sea buckthorn (*Hippophae rhamnoides*). In a particular embodiment, the step of applying the pharmaceutical agent is carried out during at least one stage of wound healing selected from the group consisting of inflammation, granulation and epithelialization. In a particular embodiment, the method comprises a step of applying a corticosteroid during the granulation stage of wound healing.

In another aspect, the invention provides a method for treating an enzymatically debrided wound bed in a subject in need thereof, the method comprising the step of applying over the wound bed a wound dressing, wherein the wound dressing comprises an open conduit polyurethane foam and hyaluronic acid or a pharmaceutically acceptable salt or derivative thereof, wherein the hyaluronic acid is disposed in dry form on the inner surfaces of the conduits within the polyurethane foam, and wherein the diameter of the conduits within the polyurethane foam is between about 300 μm and about 5000 μm, thereby treating the enzymatically debrided wound bed in the subject.

In another aspect, the invention provides a use of an open conduit polymer foam and at least one gel-forming hydrophilic polysaccharide for the preparation of a wound dressing for promoting healing of a debrided wound bed in a subject in need thereof, wherein the wound dressing comprises the hydrophilic polysaccharide disposed in dry form on the inner surfaces of the conduits within the polymer foam, and wherein the wound dressing is for application over the debrided wound bed.

In another aspect, the invention provides a use of an open conduit polyurethane foam and hyaluronic acid or a pharmaceutically acceptable salt or derivative thereof, for the preparation of a wound dressing for treating an enzymatically debrided wound bed in a subject in need thereof, wherein the wound dressing comprises the hyaluronic acid is disposed in dry form on the inner surfaces of the conduits within the polyurethane foam, and wherein the diameter of the conduits within the polyurethane foam is between about 300 μm and about 5000 μm, and wherein the wound dressing is for application over the enzymatically debrided wound bed.

Other objects, features and advantages of the present invention will become clear from the following description and drawings.

BRIEF DESCRIPTION OF THE FIGURES

FIG. 4 shows a sequence of photographs documenting treatment and healing of a second degree scald burn sustained in the forearm of an adult male. Adjacent areas of the burn were treated with either a wound dressing of the invention composed of polyurethane foam coated on the inner surfaces with hyaluronic acid (denoted ILM), or a wound dressing composed of sodium carboxymethylcellulose and ionic silver (Aquacel® Ag; denoted AqAg).

FIG. 4a shows the burn wound following rapid enzymatic debridement with Debrase®.

FIG. 4b shows Day 3 post dressing with either ILM, or with AqAg.

FIG. 4c shows Day 5 post dressing in close-up view.

FIG. 5 shows a sequence of photographs documenting treatment and healing of an inflicted standard deep burn wound in an experimental piglet system.

FIG. 5a shows the wound at day 1, immediately following burn infliction.

FIG. 5b shows the wound at day 1, following enzymatic debridement with Debrase®, 4 hours after burn infliction and then dressed with an open conduit polyurethane foam coated on the inner surfaces with hyaluronic acid to form an ILM.

FIG. 5c shows the dressed wound at day 4, showing discoloration typical of full thickness defects, and after non-adherent edges of dressing are cut away.

FIG. 5d shows the wound at day 7, following soaking the ILM with a broad spectrum bacteriostatic solution (Sulfamylon®).

FIG. 5e shows the ILM at day 9 having a clear and clean appearance.

FIG. 5f shows the ILM at day 12, showing progression of healing, and following excision of the free edges of the dressing.

FIG. 5g shows application of hyaluronic acid cream over the dressing at day 12.

FIG. 5h shows the progression of healing by day 15, when the dressing over healed wound is excised away, leaving a small adherent island over the healing full thickness wound.

FIG. 5i shows that at day 17, the dressing is peeled off the healed portion of the wound, and the central portion of the wound, not yet healed, presents as a flat clean bed.

FIG. 5j shows the wound at day 22, showing complete epithelialization.

DETAILED DESCRIPTION OF THE INVENTION

Figure 1:
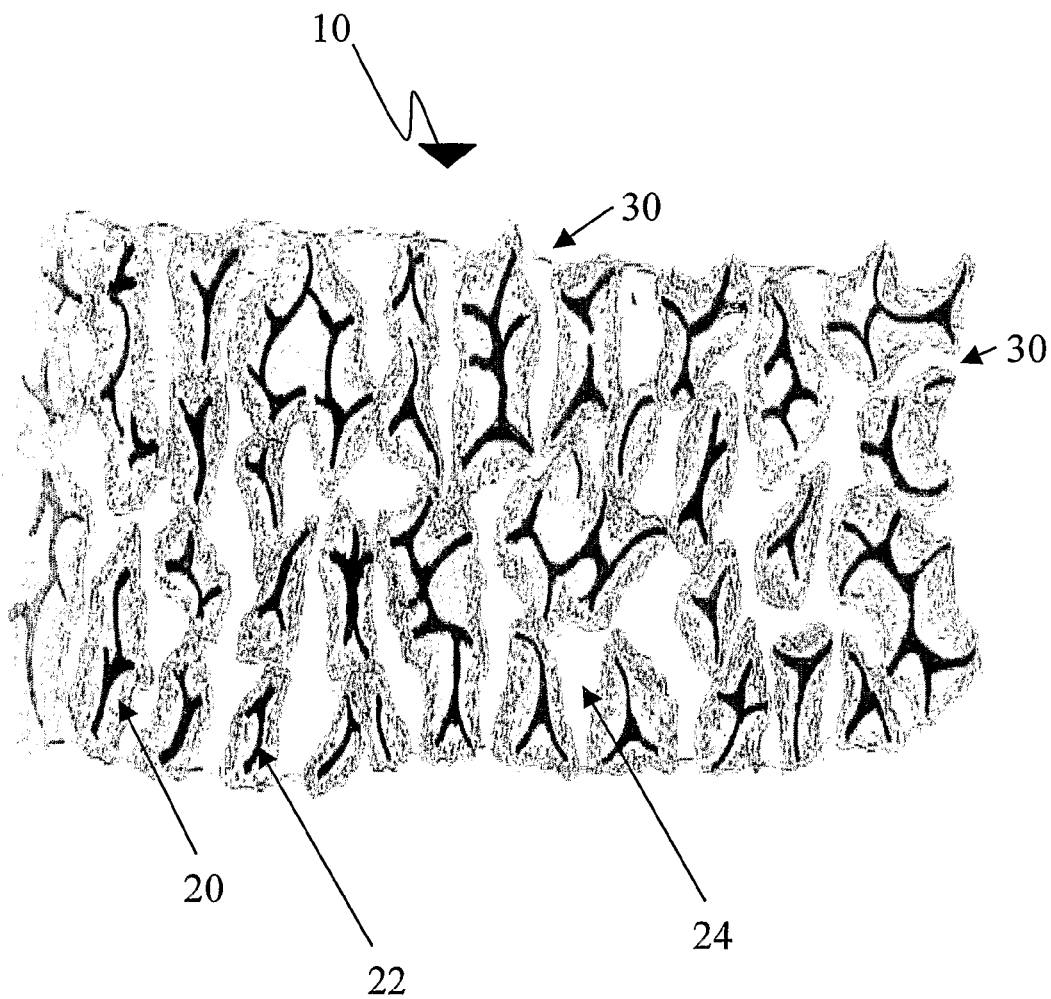
FIG. 1 is a schematic illustration of one embodiment of the wound dressing of the invention shown in cross-section.

Rapid and selective enzymatic debridement of wound sites is an emerging new technique for wound bed preparation, selectively removing dead tissue within four hours of enzyme application, and leaving healthy tissue substantially intact. Thus, the new technique spares uninjured tissues and skin (in contrast to surgical debridement), and is accomplished in a short time frame (in contrast to "conservative" non-surgical, debridement involving repeated dressings and applications of topical medication). The wound bed produced by rapid enzymatic debridement presents a different clinical picture and behavior than that produced using the aforementioned prior debridement techniques, and thus requires specifically compatible dressings which promote and optimize wound repair.

The wound dressing according to the present invention is ideally suited for application on wound beds treated by rapid enzymatic debridement, but can also be effectively used on other wound beds to create an interface layer microenvironment conducive to wound repair.

Advantageously, the wound dressing of the invention provides various capabilities, including desiccation of "weeping", discharging wounds, formation of a rich moist layer conducive to epithelialization and preservation of the raw surface, removal of exudates, and a means for delivering medicaments (e.g. antibacterial agents, growth factors, corticosteroids and trace elements) to the healing surface. Further, the invention may be used in combination with other treatment modalities, such as negative pressure or gases such as oxygen or ozone, as described for example in U.S. Patent Application Publication No. 2007/0185426.

Definitions

As used herein, the term "wound bed" refers to the uppermost visible tissue layer of a wound site.

As used herein "interface layer" refers to the raw tissue surface remaining after rapid and selective enzymatic debridement of a cutaneous necrotic wound.

As used herein "interface layer microenvironment" or "ILM" refers to the site of a enzymatically debrided wound bed enclosed by a wound dressing according to the invention.

As used herein, the term "matrix" refers to an open conduit polymer foam having a polysaccharide disposed in dry form on the inner surfaces of the conduits within the foam.

The terms "conduits", "channels", and "cells" are used herein interchangeably to refer to the compartments within a foam which interconnect one with another to form a structural network. As used herein, the terms "open conduit polymer foam" and "open cell polymer foam" interchangeably refer to a polymer foam material, for example a polyurethane foam, of any three dimensional shape, having an inner configuration in which the majority of the conduits are substantially continuous between any two external surfaces of the foam and have openings at such external surfaces. For example, open conduits in a foam slab in the shape of a cube have openings on two opposing or two adjacent sides of the cube. Thus, for example in the wound dressing of the invention, the conduits may have openings on an external surface of the foam which does not face or directly contact the wound bed and on an opposing external surface of the foam which faces or directly contacts the wound bed. In contrast, "closed conduit" or "closed cell" foams are characterized by conduits or cells within the interior of the foam which substantially lack openings at the outer surfaces of the foam.

The degree of "open-ness" of a foam may be expressed as that percentage of conduits which are substantially continuous between and have openings at any two outer surfaces of the foam.

As used herein, the term "external surface" refers to any outer surface of a foam matrix which may provide an interface with the external environment or the wound site.

As used herein, the term "opposed external surfaces" refers to a first external surface of the foam configured to face the wound bed, and a second opposing external surface of the foam which is exposed to the environment.

As used herein, "patency" refers to the state and/or degree of non-obstructedness of the conduits in a polymer foam. A high degree of patency is desirable so as to allow transmission of gases and liquids between any two outer surfaces of the foam, for example the outer surface of the foam which does not contact the wound bed and the opposing outer surface of the foam which directly contacts the wound bed.

According to particular embodiments of the invention disclosed herein, the wound dressing is fashioned from an open conduit polymer foam, and comprises a first outer surface which directly contacts the wound bed, and a second opposing outer surface which is not in direct contact with the wound bed.

As used herein, the term "surface which directly contacts the wound bed" in reference to the wound dressing of the invention, refers to a first outer surface which faces the wound bed and in general is in direct physical contact with the wound bed. A second opposing outer surface does not directly contact the wound bed, but rather is in indirect contact via the conduits forming the matrix of the polymer foam.

As used herein, the term "inner surfaces of the conduits" refers to the walls of the conduits within the polymer foam.

As used herein, the term "disposed in dry form" in reference to the hydrophilic polysaccharide means that the polysaccharide is present in dry form on the conduit walls as a result of being applied, spread, deposited, coated or dispersed thereupon. The process used for such application, spreading, deposition, coating or dispersal may employ any form of the polysaccharide, including for example, a solution, gel or powder form of the polysaccharide, and may further comprise a drying step.

As used herein the term "layer" in reference to a wound dressing refers to a continuous sheet, film or slab, of any three-dimensional shape that contains one or more materials.

As used herein the term "multi-layer" in reference to a wound dressing refers to a plurality of layers positioned one on the other, with substantially no integration between the layers, except for the interface or junction between distinct layers.

As used herein the term "dry" and variations thereof, refers to a physical state that is dehydrated or anhydrous, i.e., substantially lacking liquid. The polysaccharide in dry form of the invention preferably has less than 10% residual moisture, and more preferably less that 5% residual moisture.

The term "lyophilize" refers to the preparation of a material of composition in dry form by rapid freezing and dehydration in the frozen state (sometimes referred to as sublimation). This process may take place under vacuum at reduced air pressure resulting in drying at a lower temperature than required at full pressure.

As used herein, the term "polyurethane foam" refers to a product obtained by reacting an isocyanate or polyisocyanate with an isocyanate-reactive hydrogen containing compound, generally using foaming agents. Polyurethane foams include products obtained with water as reactive foaming agent (involving a reaction of water with isocyanate groups yielding urea linkages and carbon dioxide and producing polyureaurethane foams) and with diols, polyols, aminoalcohols and/or polyamines as isocyanate-reactive compounds.

As used herein, "hyaluronic acid" refers to any form of hyaluronic acid, including salts, mixed salts, free acids and mixtures thereof, as well as chemically modified derivatives including cross-linked forms with varying degrees of cross-linking, forms chemically linked to other compounds, and combinations thereof.

As used herein, "non-biodegradable" refers to materials that are not bioresorbable and/or do not degrade and/or do not break down into components upon interaction with a physiological environment, over a period of time from minutes to about one year, while maintaining the structural integrity of the original material. In reference to polymers, the term "non-biodegradable" means that the polymer chain is not cleaved, and that the molecular weight stays constant.

Embodiments of the Invention

The wound dressing of the invention comprises a matrix of a polymer foam having polysaccharide-coated conduits within the foam. Prior to its deployment on a wound surface, the conduit walls define unoccupied or partially unoccupied compartments or channels within the matrix. During use, the polysaccharide becomes hydrated from absorption of wound exudates and thus forms a gel and the gel expands. The expanded polysaccharide almost fully and/or partially occupies the formerly unoccupied compartments or channels, but leaves sufficient patency for transmission of gases and liquids between the two opposing external surfaces of the foam, i.e. the external surface which does not directly contact the wound bed and is exposed to the external environment, and the opposed external surface which directly contacts the wound bed. The aforementioned opposed external surfaces are also referred to herein respectively as the "outer facing" and "inner facing" surfaces of the foam, with reference to their position relative to the wound surface.

Figure 2:
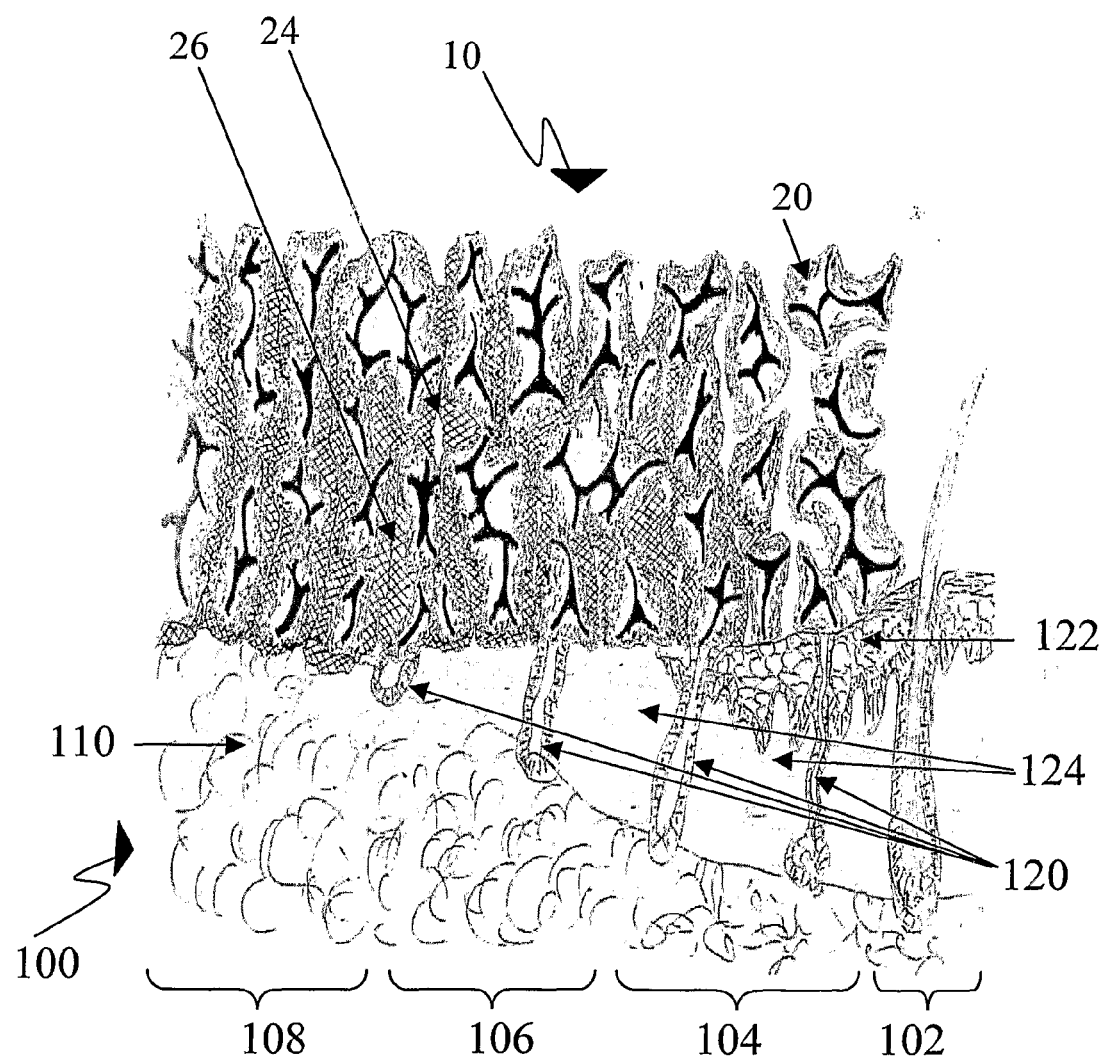
FIG. 2 is a schematic illustration of application of the wound dressing of FIG. 1 to a mixed depth wound bed, shown in cross-section.

FIG. 1 illustrates a cross-sectional view of a wound dressing (10) of the invention. The inner surfaces (22) (or "walls") of the polymer foam define the conduits (24). The hydrophilic polysaccharide in dry form (20) is disposed on the inner surfaces and on opposing external surfaces of the foam to form a matrix. Unoccupied spaces remain within the conduits. Conduit openings (30) are present at the external surfaces of the foam. FIG. 2 illustrates a cross-sectional view of a wound dressing (10) of the invention in place over a mixed-depth wound bed (100). The wound bed comprises intact skin (102) with preserved epidermis (122); a region with primary epidermal damage (104); a region with secondary progressing dermal damage (106); and a tertiary full-thickness defect (108). Regions (104) and (106) comprise some preserved skin appendages (120) and dermis (124), while region (108) has exposed subcutaneous structures, in particular adipose tissue (110) with few epidermal remnants in the bottom of skin appendages. Due to absorption of liquids from the wound bed, the hydrophilic polysaccharide within most areas of the wound dressing is in an expanded form (26). Unoccupied spaces (24) remain within conduits containing the expanded polysaccharide (26) but are narrowed. In fewer areas within the wound dressing, the hydrophilic polysaccharide remains in dry form (20).

Figure 3:
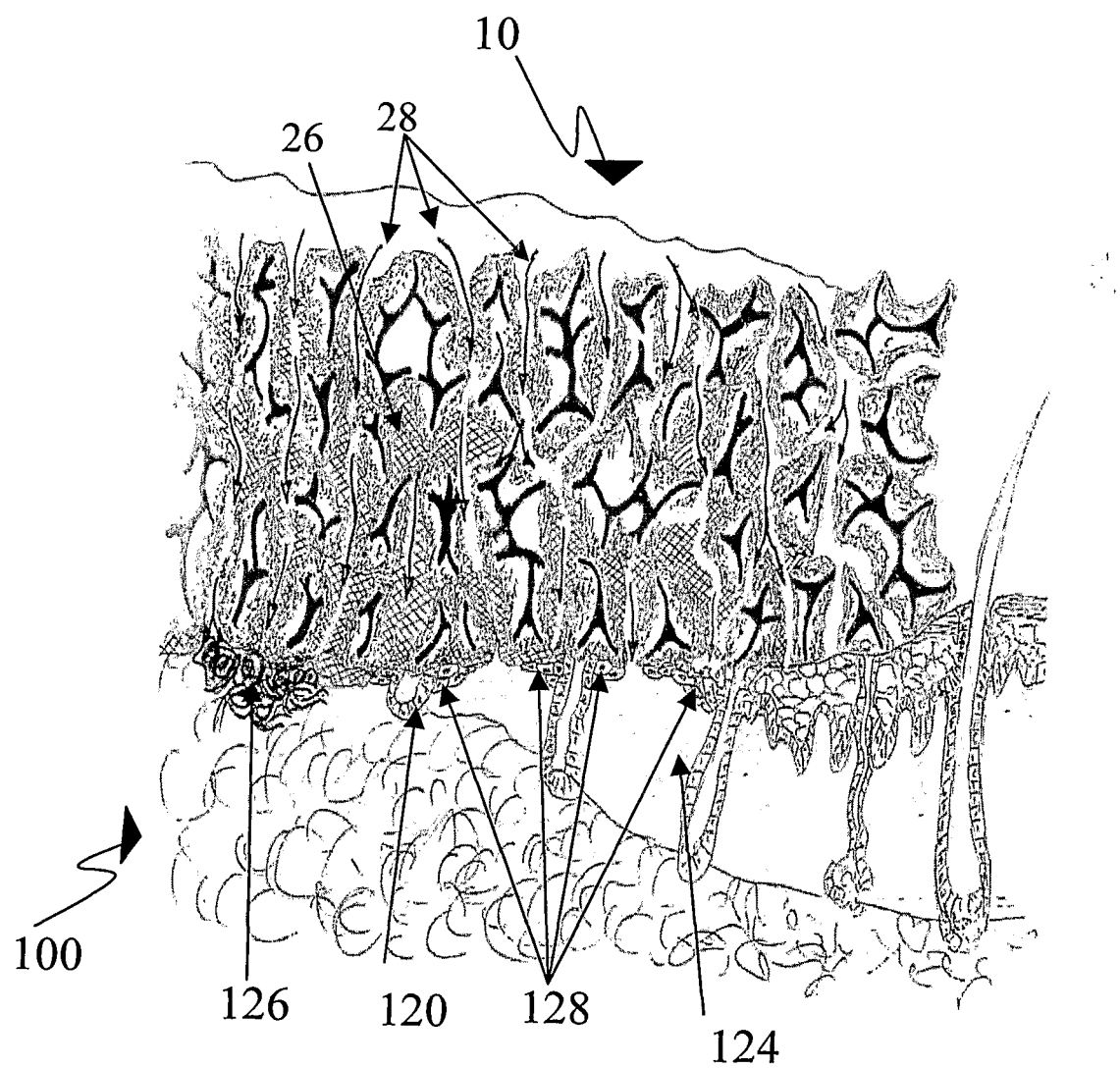
FIG. 3 is a schematic illustration of the wound healing process of the treated wound bed shown in FIG. 2.

FIG. 3 illustrates progression of the wound healing process in the dressed wound shown in FIG. 2. In the wound bed (100), the epithelialization front (128) originating from epidermal edges and skin appendages (120) advances over preserved dermis (124). Granulation tissue (126) forms over non-epithelizing surface. Pharmaceutical agents (28) applied to the outer surface of the wound dressing matrix percolate through the hyaluronic acid-occupied conduits (26).

In a particularly preferred embodiment, the wound dressing is a single layer dressing comprising polyurethane foam and hyaluronic acid, having the configuration shown in FIG. 1 and as described in Experimental Example 1. Further, the wound dressing is preferably substantially devoid of an adhesive material, such as epoxy compounds and other adhesive materials well known in the art for use in wound coverings and dressings.

Polymer Foam

The present invention provides a wound dressing for creating an interface layer microenvironment in a wound bed, the wound dressing comprising an open conduit polymer foam and at least one polysaccharide.

A particularly preferred open conduit polymer foam comprises open conduit polyurethane. In a particular embodiment, the polymer consists essentially of open conduit polyurethane. The polyurethane may be a polyester polyurethane or a polyether polyurethane, and/or may be a cross-linked polyurethane.

Polyurethane foams produced by the reaction of a polyol with a polyisocyanate generally in the presence of a catalyst, surfactant and blowing agent are well known in the art, as disclosed for example, in *Polyurethane and Related Foams: Chemistry and Technology* (2006) by K. Ashida, CRC Press.

Briefly, a polyisocyanate i.e. a molecule of formula R—(N=C=O)$_{n \leq 2}$ having two or more isocyanate functional groups, and a polyol i.e. a molecule of formula R'—(OH)$_{n \leq 2}$ having two or more hydroxyl functional groups, form a polymer reaction product of formula —RNHCOOR'-containing urethane linkages.

Suitable polyisocyanates can be aromatic, such as diphenylmethane diisocyanate (MDI) or toluene diisocyanate (TDI); or aliphatic, such as hexamethylene diisocyanate (HDI) or isophorone diisocyanate (IPDI). Also suitable are polymeric isocyanates, such as polymeric diphenylmethane diisocyanate, which is a blend of molecules with two-, three-, and four- or more isocyanate groups. Isocyanates can be further modified by partial reaction with a polyol to form a prepolymer.

The polyol may be a diol, triol, or of higher functionality, generally formed by base-catalyzed addition of propylene oxide (PO), ethylene oxide (EO) onto a hydroxyl or amine containing initiator, or by polyesterification of a di-acid, such as adipic acid, with glycols, such as ethylene glycol or dipropylene glycol (DPG). Polyols extended with PO or EO are polyether polyols. Polyether polyols having a functionality of at least 2.0 are known to be suitable for producing flexible polyurethane foams. The term "polyether polyol" includes linear and branched polyethers (having ether linkages), and containing at least two hydroxyl groups. Polyester polyols are polyols formed by polyesterification. The choice of initiator, extender, and molecular weight of the polyol to influence the physical properties of the polyurethane polymer are within the ability of one of average skill in the art.

The polymerization reaction may be catalyzed by tertiary amines, such as dimethylcyclohexylamine, or by organometallic compounds, such as dibutyltin dilaurate or bismuth octanoate, as is known in the art.

To produce a polyurethane foam, blowing agents such as water, are used to create carbon dioxide gas upon reaction with the isocyanate, which fills and expands cells created during the mixing process, thus creating a foam.

In a technique known as frothing, a blowing agent having a boiling point below room temperature is used so that foaming occurs even before any substantial reaction between the reactants or before any heat is evolved.

A surfactant is often used to control the amount and quality of the foamed polyurethane obtained, for example to maximize open cell content.

Chain extenders and cross linkers, generally low molecular weight hydroxyl and amine terminated compounds, may be used to influence the polymer morphology of polyurethane foams, as is known in the art.

Methods of producing polyurethane foams are disclosed for example, in U.S. Pat. Nos. 3,194,773; 3,383,351; 3,454,505; 3,978,266; 3,975,567; 3,993,576; 4,385,133; 4,670,477; 4,950,694, and 4,863,976.

For use in the invention, the polyurethane foam may be one that is produced using commercially available polyurethane prepolymers, such as those marketed under the trade name Hypol® (Dow). Alternately, the prepared polyurethane foam may be purchased from a commercial supplier.

Alternative polymer foam materials may be used for the wound dressing, for example cellulose derivatives, polyolefins, polyvinylchloride, polyvinylfluoride, poly(vinylimidazole), polyacrylates, ethylene-vinyl acetate copolymers, polystyrenes, and polyethylene oxide. Any suitable blends or copolymers of these materials can also be used It is generally preferred that the polymer foam matrix is a synthetic or semi-synthetic material. A preferred polymer foam for the invention is substantially non-biodegradable.

According to the invention, the polymer foam has a conduit diameter of at least 300 µm. In a particular embodiment, the conduit diameter is between about 300 µm and about 5000 µm. In particular embodiments, the conduit diameter is between about 300 µm and about 1000 µm, or between about 1000 µm and about 3000 µm, or between about 1000 µm and about 4000 µm. In a particular embodiment, the diameter of the conduits is greater than 5000 µm. In a particular embodiment, the diameter of the conduits is about 500 µm. Each possibility is a separate embodiment of the invention.

It is to be understood that in the wound dressing, the effective conduit diameter may be reduced due to the deposition of the polysaccharide in dry form onto the inner surfaces of the conduits. However, prior to use the polysaccharide-coated inner surfaces still define unoccupied or partially unoccupied compartments or conduits within the matrix. During use, the polysaccharide becomes hydrated from absorption of wound exudates and thus expands, so as to fully and/or partially occupy the formerly unoccupied compartments or conduits, as illustrated in FIGS. 2 and 3.

Without wishing to be bound by any particular theory, it is believed that the large size of the conduits in the polymer foam matrix combined with the hydrophilic polysaccharide contained therein provides a unique and synergistic effect, rendering the wound dressing significantly advantageous over prior art products. The large conduit size is able to accommodate a considerable quantity of the hydrophilic polysaccharide that serves as an interface and pathway between the liquids absorbed from the wound surface and the medicaments applied onto the external surface of the dressing. The large conduit size allows passage of liquids as well as viscous materials such as creams and ointments, and even polysaccharide if its replenishment is required. The liquids absorbed from the wound surface help to adhere the dressing to the wound bed. The hydration of the polysaccharide is balanced by the evaporation or absorption by optional additional absorbing dressing (i.e. cotton gauze) from the external surface, transmission through the conduits and available fluids originating in the wound or supplied on the external surface. Furthermore, the hydrated dressing-wound interface serves as an upper surface under which the epithelial front advances during the epithelialization stage in the wound healing process, as illustrated in FIG. 3. This hydrated dressing-wound interface serves also as a modulating surface to control an undesired formation of granulation tissue.

In contrast, an occlusive dressing, even that provided by a large conduit (e.g. ≤200 µm) open-cell polymer foam lacking a hydrophilic polysaccharide, exhibits many disadvantages. Such an inert matrix can become saturated with and filled by exudates, but it is entirely incapable of actively drawing liquids and exudates from the wound bed. The stagnant exudates coagulate rapidly and provide a breeding ground for rapid microbial proliferation and infection under the dressing surface. Furthermore, such a dressing will not adhere to the wound, nor will it allow passage of substances from the external surface through the dressing. Another disadvantage is that healing tissues may grow into the matrix, with the epithelial cells adhering and propagating on the walls of the conduits, imbedding the dressing onto the wound. When the conduits start to be too wide for the cells to form a solid cellular column, they behave as an open tissue culture to form a generally flat, epithelializing or granulating layer.

Similarly, a small conduit (e.g. ≤200 μm) open-cell polymer foam lacking a hydrophilic polysaccharide will not adhere to the wound and cannot facilitate passage of liquids from the wound or substances from the external surface through the dressing to the wound.

Generally, the synthetic polymer foam matrix is in the form of a sheet having a thickness of about 2 to about 12 mm. In a particular embodiment, the open conduit polymer foam has a thickness of about 4 to about 8 mm. As used herein, the thickness refers to the dimension between the opposing outer surfaces of the foam matrix, measured prior to hydration. That is, the width of the foam between the outer surface which is not intended to directly contact the wound bed and that outer surface which is intended to directly contact the wound bed.

In a particular embodiment, the open conduit polymer foam has an absorption of at least 50% on a weight per weight (w/w) basis. In a particular embodiment, the absorption of the open conduit polymer foam is greater than 100% (w/w). In a particular embodiment, at least 75% of the conduits in the polymer foam are open i.e. continuous between and having openings at the opposing outer surfaces of the foam. In a particular embodiment, substantially 100% of the conduits in the polymer foam are open. In a particular embodiment, the polymer foam has from about 200 to about 500 conduit openings per $cm^2$. In a particular embodiment, the polymer foam has about 300 conduit openings per $cm^2$. As used herein, the number of conduits per $cm^2$ refers to the number of conduit openings per unit surface area on any outer surface of the foam, or an average thereof.

In a particular embodiment, the polymer foam has a density between about 0.1 and about 0.4 $g/cm^3$, such as between about 0.1 and about 0.2 $g/cm^3$, or between about 0.1 and about 0.15 $g/cm^3$.

In a particular embodiment, the polymer foam has an air transmission rate of between about 30 and about 90 liter/min. In a particular embodiment, the air transmission rate is about 60 liter/min. As used herein, the air transmission rate refers to that rate of air transfer across a 100 mm thickness of material having a surface area of 100 $mm^2$ under application of 5 atmospheric pressures.

Polysaccharides

The polysaccharide selected should be sufficiently hydrophilic so as to absorb liquid and exudates which seep from the wound bed. Suitable polysaccharides include, but are not limited to: hyaluronic acid, a sulfated glycosaminoglycan, chitosan, alginate, hydroxyethyl cellulose, carboxymethyl cellulose, a cellulose derivative, pectin, gum arabic, starch, pharmaceutically acceptable salts thereof and combinations thereof.

In a currently preferred embodiment, the polysaccharide is hyaluronic acid or a pharmaceutically acceptable salt or derivative thereof. The hyaluronic acid may be cross-linked or non-cross-linked. Hyaluronic acid (also referred to as hyaluronate or hyaluronnan), is a linear polysaccharide composed of a disaccharide-repeating unit of N-acetyl-D-glucosamine and D-glucuronic acid linked by β1-4 and β1-3 linkages. Hyaluronic acid is a ubiquitous component of the extracellular matrix of all connective tissues, and is present, for example, in umbilical cord, vitreous humor, synovial fluid, rooster combs and skin. Hyaluronic acid is also produced as an extracellular secretion in group A and C hemolytic streptococci. Hyaluronic acid has a range of naturally occurring molecular weights, ranging from several thousand to over 10 million daltons. The unique viscoelastic properties of hyaluronic acid combined with its biocompatibility and immunoneutrality, has led to its use in a variety of clinical applications, including wound healing and control of inflammation.

The hyaluronic acid used in the wound dressing of the present invention may be derived from any known source, using techniques known in the art, as long as the hyaluronic acid is of sufficient purity and viscosity to be therapeutically effective in the wound dressing disclosed herein. Furthermore, the hyaluronic acid may be chemically modified, such as by cross-linking and further may be linked or associated with other moieties including drugs, additional polymers and other functional compounds.

Hyaluronic acid may be derived from: rooster combs, as described for example, in U.S. Pat. Nos. 4,141,973 and 4,303,676; from *Streptococcus* bacterial culture, as described for example, in U.S. Pat. Nos. 4,517,295; 4,780,414; 4,784,990, and 4,946,780; or from recombinant DNA technology, as described for example, in U.S. Pat. No. 5,015,577. Additional methods of obtaining highly pure hyaluronic acid and its salt forms, isolation techniques, and analytical methods for testing purity are disclosed, for example, in U.S. Pat. Nos. 3,396,081; 4,736,024, and 4,808,576. The hyaluronic acid may be of very high molecular weight i.e. 9-25 million daltons, as disclosed for example in U.S. Pat. No. 6,610,666.

Various hyaluronic acid derivatives obtained by chemical modification and/or crosslinking of native hyaluronic acid may be used in the present invention. The principle targets for chemical modification of hyaluronic acid are the hydroxyl and carboxyl functions. Modifications via the hydroxyl functions are primarily useful for the preparation of crosslinked hyaluronic acid by reactions with bifunctional cross linkers, e.g. divinyl sulfone and diglycidyl ethers, as disclosed for example, in U.S. Pat. Nos. 4,582,865 and 4,713,448.

Modifications of the carboxylic functions are useful for the introduction of pendant functionalities, which can further be used to obtain crosslinked products or as sites for the covalent attachment of various chemicals, e.g. drugs and biochemical reagents. Those modifications are generally made using hydrazides or amines. Activation of the carboxylic functions of hyaluronic acid towards nucleophilic attack by hydrazides or amines, in aqueous media, is mainly performed by the use of water soluble carbodiimides, especially 1-ethyl-3-[3-dimethylaminopropyl]carbodiimide (EDC). Methods for performing such activation are disclosed for example, in U.S. Pat. Nos. 5,616,568; 5,874,417, and 6,630,457. Amide derivatives of hyaluronic acid may also be employed, as disclosed for example, in International Patent Publication No. WO 00/01733.

The gel disclosed herein may comprise a drug delivery gel based on cross-linked hyaluronic acid and a hydrophilic polymer such as a polysaccharide, protein or glycoprotein, as disclosed for example in U.S. Pat. No. 5,128,326.

The dry hyaluronic acid disposed upon the inner surfaces of the conduits of the wound dressing is generally in a salt form, such as sodium hyaluronate. Other salts of hyaluronic acid are also contemplated, including those formed with alkali metals, alkaline earth metals, magnesium, aluminum, ammonium and substituted ammonium ions.

It is to be understood that there is no particular upper or lower limitation on the molecular weight of the hyaluronic acid or hyaluronate salt used, as long as it is of sufficient molecular weight and viscosity to take on a gel-like consistency upon contact with liquid and have a high liquid retention capability.

It is to be understood that there is no particular upper or lower limitation on the purity of the hyaluronic acid or hyaluronate salt used, as long as it is sufficiently pure so as not to promote microbial growth and it may contain non-dissolvable materials and particles, oils, waxes and solids.

Methods for Producing the Wound Dressing

In the wound dressing of the invention, the polysaccharide is disposed in dry form on the inner surfaces of the conduits within the foam, and optionally upon at least one external surface of the foam.

For preparing the wound dressing, the polysaccharide is disposed in dry form on the inner surfaces of the conduits of the foam by a method comprising: (i) applying the polysaccharide in the form of a solution or gel to at least one outer surface of the foam so as to cover said outer surface; and (ii) subjecting the foam obtained in (i) to drying under vacuum. The drying step may comprise vacuum desiccation or lyophilization.

The process may further comprise an additional step: (iii) impregnating the hydrophilic polysaccharide applied in (i) into the open conduits within the polymer foam, wherein (iii) is carried out prior to (ii). To carry out step (iii) the polysaccharide is subjected to forces that promote its introduction throughout the conduits. Step (iii) may comprise an operation selected from the group consisting of centrifugation, application of negative pressure, application of positive pressure and application of vacuum. Step (iii) is carried out prior to the drying step of (ii). Application of vacuum may be used for both steps (ii and iii). For example, a short relatively strong burst of vacuum may be initially applied as step (iii) so as to impregnate the polysaccharide throughout the conduits. Afterwards, a longer and gentler period of vacuum may be used as step (ii) to dry the polysaccharide onto the conduit walls.

In a particular embodiment, the amount of the hydrophilic polysaccharide applied to the external surface of the polymer foam in (i) is from about 0.1 to about 20.0 milligram (mg) per $cm^2$ of said external surface of the polymer foam. In a particular embodiment, the amount of the hydrophilic polysaccharide applied is from about 1.0 to about 10.0 mg per $cm^2$ of said external surface of the polymer foam.

In the produced foam matrix, the polysaccharide is disposed in dry form on the inner surfaces of the conduits within the foam, and on at least one of the opposing external surfaces of the foam. In a particular embodiment, the polysaccharide is disposed in dry form on the inner surfaces of the conduits within the foam, and on the outer surface of the foam which directly contacts the wound bed. In another particular embodiment, the polysaccharide is disposed in dry form on the inner surfaces of the conduits within the foam, and on both opposing outer surfaces of the foam.

In a particular embodiment, the hydrophilic polysaccharide is present in an amount of from about 0.001 gram to about 1.0 gram per $cm^3$ of polymer foam. In particular embodiments, the hydrophilic polysaccharide is present in an amount of from about 0.001 gram to about 0.01 gram per $cm^3$ of polymer foam; or from about 0.01 gram to about 0.1 gram per $cm^3$ of polymer foam; or from about 0.1 gram to about 1.0 gram per $cm^3$ of polymer foam.

For preparing a foam matrix comprising polyurethane foam and hyaluronic acid, the method may comprise: (i) applying hyaluronic acid or a pharmaceutically acceptable salt or derivative thereof in the form of a solution to at least one external surface of an open conduit polyurethane foam so as to cover said external surface; and (ii) subjecting the foam obtained in (i) to drying under vacuum.

As described above, an additional step (iii) may be used to impregnate the hyaluronic acid throughout the conduits prior to drying step (ii). In particular embodiments, step (iii) comprises application of vacuum. The embodiment in which different vacuum forces are used to carry out steps (iii) and (ii) is described in Experimental Example 1.

In a particular embodiment, the amount of hyaluronic acid applied to the external surface of the polyurethane foam in (i) is from about 1.0 to about 10.0 mg per $cm^2$ of said external surface of the polyurethane foam.

The drying of the hyaluronic acid in (step (ii) is preferably carried out in a slow manner. This process is aimed at slow evaporation of water from the entire hyaluronic acid within the conduit, so as to dry and shrink the hyaluronic acid onto the conduit walls as a uniform deposit without forming clumps that can obstruct the conduits. Variations of the vacuum desiccation process described in Experimental Example 1 may be used, such as by varying the duration of the drying process in accordance with the concentration of the hyaluronic acid, the size of the conduits, and the thickness of the foam. For example, foam having with larger conduits may require higher vacuum and/or longer drying time than foam with smaller conduits. are, slower the process should be. Similarly, thicker foam may require extended drying conditions compared to a thinner foam.

In a currently preferred embodiment, the wound dressing comprises open conduit polyurethane foam wherein the diameter of the conduits is between about 300 μm and about 5000 μm, and further having hyaluronic acid disposed in dry form on the inner surfaces of the conduits within the polyurethane foam and on one of the opposing outer surfaces of the polyurethane foam. It is particularly preferred that the hyaluronic acid is disposed in dry form on the inner surfaces of the conduits within the foam, and on the outer surface of the foam which directly contacts the wound bed. In a particular embodiment, the hyaluronic acid is disposed in dry form on the inner surfaces of the conduits within the foam, and on both opposing outer surfaces of the foam.

In a particular embodiment, the wound dressing comprising polyurethane foam and hyaluronic acid is a single layer dressing.

The hyaluronic acid may be present in an amount of from about 0.001 gram to about 0.01 gram per $cm^3$ of polyurethane foam. For example, the hyaluronic acid is present in an amount of about 0.001, 0.002, 0.003, 0.004, 0.005, 0.006, 0.007, 0.008, 0.009 or 0.1 gram per $cm^3$ of polyurethane foam. In a particular embodiment, the hyaluronic acid is present in an amount of about 0.5 gram per $cm^3$ of polyurethane foam. In a particular embodiment, the conduits of the polyurethane foam have a diameter of about 500 μm. In a particular embodiment, there are about 200 to about 500 conduit openings per $cm^2$ of outer surface area of the foam.

The wound dressing is preferably provided in sterile form within a packaging material, conveniently in single unit or a multi-unit format. The wound dressing may further be provided in a vacuum package, in particular to maintain the polysaccharide in dry form prior to use. In a particular embodiment, the wound dressing is substantially devoid of an adhesive material.

Pharmaceutical Ingredients

The wound dressing may further comprise a pharmaceutical ingredient or agent selected from the group consisting of: a corticosteroid, a growth factor, a bacteriocidal agent, an antibiotic, and a plant extract. One non-limiting example of a plant extracts one derived from sea buckthorn (*Hippophae*

*rhamnoides*). In a particular embodiment, the pharmaceutical ingredient is disposed upon the outer surface of the foam which does not directly contact the wound bed but due to unique characteristics of the matrix the ingredient can percolate through the matrix onto the wound surface. In a particular embodiment, the pharmaceutical ingredient is in a form selected from the group consisting of a solution, an oil, a foam, a gel, a cream and an ointment.

Corticosteroids include, but are not limited to betamethasone dipropionate, diflorasone diacetate, halobetasol propionate, amcinonide, desoximetasone, triamcinolone acetonide, flucinolone acetonide, diflorasone diacetate, halcinonide, flucinonide, and combinations thereof.

Growth factors include, but are not limited to fibroblast growth factor (FGF), platelet-derived growth factor (PDGF), transforming growth factor beta (TGF-β), transforming growth factor-alpha (TGF-α), beta-thromboglobulin, insulin-like growth factors (IGFs), tumor necrosis factors (TNFs), interleukins (e.g., IL-1, IL-2, etc.), colony stimulating factors (e.g., G-CSF; GM-CSF, erythropoietin), nerve growth factor (NGF), and interferons (e.g., IFN-alpha, IFN-beta, IFN-gamma). The growth factor may be native or synthetic (i.e. chemically or recombinantly produced), and may be of human or other mammalian type. Synthetic analogs of the factors, including small molecular weight domains, may be used provided they exhibit substantially the same type of activity as the native molecule. Such analogs may be made by conventional genetic engineering techniques, such as via expression of synthetic genes or by expression of genes altered by site-specific mutagenesis. The growth factor may be incorporated into the wound dressing in its native form (e.g. platelets in the case of PDGF), or as crude or partially purified preparations. Alternatively, the factors may be incorporated in a substantially pure form, substantially free of contaminating materials.

Bacteriocidal agents include, but are not limited to chlorhexidine gluconate, benzalkonium chloride, iodine, urea perhydrate, triclosan, a silver-containing compound (e.g. colloidal silver, silver nitrate), mafenide acetate, sodium hypochlorite and salicylic acid.

Antibiotics include, but are not limited to sulfa drugs, penicillins, cephalosporins, tetracyclines, erythromycins, aminoglycosides, polypeptide antibiotics, fluoroquinolones, chloramphenicol, clindamycin, rifampin, spectinomycin, vancomycin, bacitracin, cyclosporine, dapsone, ethambutol, ethionamide, isoniazid, nitrofurantoin, pyrazinamide, and trimethoprim.

Plant extracts include, but are not limited to evening primrose oil, soya oil, tea tree oil, coconut oil, jojoba oil, extracts derived from camomile, sea buckthorn or aloe vera, and mixtures thereof.

If included, the additional polysaccharide may be the same as or different from the hydrophilic polysaccharide that is disposed in dry form into the conduits and upon the surfaces thereof. The additional polysaccharide may be selected without limitation, from hyaluronic acid, a sulfated glycosaminoglycan, chitosan, alginate, hydroxyethyl cellulose, carboxymethyl cellulose, a cellulose derivative, pectin, gum arabic, starch, pharmaceutically acceptable salts thereof and combinations thereof. The additional polysaccharide may be the same chemical entity as that disposed in dry form on the foam surfaces, but it may be in a different form. For example, hyaluronic acid may be the polysaccharide disposed in dry form on the inner surfaces of the conduits. As required during the healing process, hyaluronic acid in the form of a gel or cream, or in combination with hydrophobic materials in particulate form (e.g. oily micelles, waxes) may be applied to the external surface of the wound dressing.

Additional components may also be present in the wound dressing, for example humectants to assist in maintaining moisture in the ILM. Suitable humectants include glycerol, sorbitol, soft paraffin, urea creams, lanolin, sodium pyrrolidone carboxylate, gamma linolenic acid, and combinations thereof.

In addition, the polysaccharide and the pharmaceutical ingredient may be formulated with a pharmaceutically acceptable excipient, such as a hydrophobic excipient. In a particular embodiment, the hydrophobic excipient is in particulate form. In a particular embodiment, the excipient is selected from the group consisting of an oil, a micelle and a wax. Such excipients may be advantageously included with the polysaccharide in dry form in order to delay evaporation and introduce oil-based active medicaments. Solid particles with biological or surface activities may be mixed into the polysaccharide exerting their activity when coming in contact with the wound when the polysaccharide is dissolved.

Method for Treating a Debrided Wound Bed

The invention further provides a method based on the ILM for treating a debrided wound bed in a subject in need thereof, the method comprising the step of applying over the wound bed a wound dressing, wherein the wound dressing comprises an open conduit polymer foam and at least one gel-forming hydrophilic polysaccharide wherein the hydrophilic polysaccharide is disposed in dry form on the inner surfaces of the conduits within the open conduit foam. It is particularly preferred that the conduits forming the matrix of the foam have a diameter of at least 300 μm.

As used herein, the term "treating a debrided wound bed" encompasses promoting healing and re-epithelialization of the wound bed.

The hydrophilic polysaccharide may also be deposited on one or both of the outer surfaces of the foam i.e. the surface which directly contacts the wound bed, and that which does not contact the wound bed.

The currently preferred wound dressing comprises open conduit polyurethane foam and hyaluronic acid, wherein the diameter of the conduits within the polyurethane foam is between about 300 μm and about 5000 μm, and wherein the hyaluronic acid is disposed in dry form on the inner surfaces of the conduits of the polyurethane foam. Additional embodiments of the wound dressing are as hereinbefore described. The method may be carried out an a wound bed that has been debrided by any means, including surgical, enzymatic, chemical, and autolytic debridement techniques, and combinations thereof. Surgical debridement involves excision of clinically diagnosed dead tissues, and is terminated at a point when the surgeon judges that the wound bed is clean, usually on the basis of the bleeding pattern.

Enzymatic debridement involves the application of proteolytic and optionally other exogenous enzymes to a wound surface to break down necrotic tissue. Enzymatic debridement may be a relatively slow process, carried out over a period of a number of weeks in combination with other topical preparations, soakings and repeated dressings. Alternately, rapid enzymatic debridement can be accomplished using multi-enzyme products, for example, those extracted from the stem of the pineapple plant, as disclosed for example in WO 98/053850 and WO 2006/0006167, and as provided in the product marketed under the trade name Debrase®. A procedure for enzymatic debridement generally utilizes an enzyme such as bromelain derivatives, debridase, collagenase, papain derivatives, streptokinase, sutilains, fibrinolysin, deoxyribonuclease, krill derivatives, trypsin or combinations thereof.

Autolytic debridement relies on enhancing the natural process of selective liquefaction, separation and digestion of necrotic tissue and eschar from healthy tissue that occurs in wounds due to macrophage and endogenous proteolytic activity. This is achieved by the use of occlusive, semi-occlusive or moist interactive dressings.

The origin of the wound bed to be treated by the method of the invention may be a chronic wound or an acute wound. Chronic wounds include but are not limited to venous leg ulcers, pressure ulcers, and diabetic foot ulcers, Acute wounds include but are not limited to burns, traumatic injuries, amputation wounds, skin graft donor sites, bite wounds, frostbite wounds, dermabrasions, and surgical wounds.

Burns which may be treated by the method of the invention include full-thickness and partial-thickness burns.

In a particular embodiment, the step of applying the wound dressing is carried out in the absence of an adhesive material. It is to be noted that a conventional adhesive material is generally not required since the wound dressing will remain adhered to the wound bed.

According to the invention, the wound dressing is maintained over the wound bed for a period of at least one week. In particular embodiments, the wound dressing is maintained over the wound bed for a period of up to 2 weeks, or for a period of up to 4 weeks. In one embodiment, the wound dressing is maintained over the wound bed until epithelialization is completed. The method may further comprise a step of applying a pharmaceutical ingredient in a form selected from the group consisting of a solution, an oil, a foam, a gel, a cream and an ointment, to the external surface of the wound dressing which does not directly contact the wound bed. The pharmaceutical ingredient may be selected from a corticosteroid, a growth factor, a bacteriocide, an antibiotic, a silver-containing compound, an additional polysaccharide and a plant extract, embodiments of which are as hereinbefore described. The step of applying the pharmaceutical ingredient may be carried out during a selected stage of wound healing for example, inflammation, granulation or epithelialization. It may be particularly beneficial to apply a corticosteroid at the granulation stage of healing.

Wound healing is the body's natural process of regenerating dermal and epidermal tissue. The process involves a series of complex biological events which overlap in time, but may be artificially categorized into various wages. In the inflammation stage, bacteria and debris are phagocytized and removed, and factors are released that cause the migration and division of cells involved in the proliferative phase. In granulation tissue formation, a new, provisional extracellular matrix is formed upon the production of collagen and fibronectin. An excessive granulation phase may be transformed into a heavy scar. In the epithelialization stage, epithelial cells migrate across the wound bed to cover it and form epidermis. The epithelial cells originate in the epidermal edges at the periphery of the wound and in the preserved epidermal adnexae (hair folicles, sweat and sebaceous glands) in the preserved dermis. The epithelialization process depends on a sufficient epithelial cell foci, an adequate dermal bed and the proper moisture and guiding surface.

The invention further provides a method for treating an enzymatically debrided wound bed which comprises a step of applying over the wound bed a wound dressing, wherein the wound dressing comprises an open conduit polyurethane foam and hyaluronic acid, or a pharmaceutically acceptable salt or derivative thereof, wherein the diameter of the conduits within the polyurethane foam is between about 300 µm and about 5000 µm, and wherein the hyaluronic acid is disposed in thy form on the inner surfaces of the conduits of the polyurethane foam.

The invention further provides a use of a an open conduit polymer foam and at least one hydrophilic polysaccharide for the preparation of a wound dressing for treating a debrided wound bed in a subject in need thereof, wherein the wound dressing comprises the hydrophilic polysaccharide disposed in dry form on the inner surfaces of the conduits of the open conduit polymer foam, and wherein the wound dressing is for application over the debrided wound bed.

The invention further provides a use of an open conduit polyurethane foam and hyaluronic acid for the preparation of a wound dressing for treating an enzymatically debrided wound bed in a subject in need thereof, wherein the diameter of the conduits within the polyurethane foam is between about 300 µm and about 5000 µm, and wherein the hyaluronic acid is disposed in dry form on the inner surfaces of the conduits of the polyurethane foam, and wherein the wound dressing is for application over the enzymatically debrided wound bed.

EXAMPLES

The following generalized examples illustrate the versatility of a wound dressing comprising large cell open conduit polyurethane foam coated on the inner surfaces with hyaluronic acid according to the invention in treating wounds of varying severity.

General Example 1

Treatment of a Clean, Viable Dermal Wound Bed

The serum excreted at the wound surface advances along the conduit wall, absorbed by the hyaluronic acid therein, hydrating it completely or partially (as depicted in FIG. 2) depending on the fluid quantity (moisture) at the wound surface. The moistened hyaluronic acid prevents desiccation of the healing wound enhancing its epithelialization that is guided by the dressing surface. The complex of hyaluronic acid and fibrin in the excreted fluids adheres the dressing to the wound, forming an "artificial, reinforced scab" preventing propagation of any infection foci. As the epithelialization progresses (usually on the dermal remnants) as depicted in FIG. 3, the keratinized epidermal layer detaches the wound dressing from the wound. The detached wound dressing areas can be sheared off by scissors. The adherent wound dressing is left on place allowing early wound care in outpatient conditions. As long as this "artificial scab" exists the dressing maintains its original color and appearance. If a non-healing wound persists beyond hydration potential of the hyaluronic acid (usually in the case of a full thickness defect), a wet, darker discoloration appears area due to change of the excreted fluids. This can be used as a diagnostic marker for treatment change. In order to avoid granulation tissue formation, corticosteroid solution or cream can applied on the surface of the wound dressing, seeping through to the wound surface (as depicted in FIG. 3). If the dressing dries and the area is small, the wound dressing may be kept in place until healing (epithelialization) is completed. If the dressing continues to change appearance, the discolored area can be excised to allow direct care (i.e. grafting) of the wound. In a long standing dressing (>one week) it is possible to add hyaluronic acid to the wound dressing by applying it in an aqueous solution on the external surface of the dressing.

General Example 2

Treatment of a Wound Bed with Partially Persistent Eschar or Light Contamination As described in General Example 1, the serum excreted at the wound surface advances along the conduit wall, absorbed by the hyaluronic acid, hydrating it completely or partially (as depicted in FIG. 2), depending of the fluid quantity (moisture) at the wound surface. The moistened hyaluronic acid prevents desiccation of the healing wound enhancing its epithelialization that is guided by the dressing surface. The moist environment together with the normal inflammatory reaction promote the maceration of the eschar remnants ("autolysis") and resolution of the contaminated foci. The autolysis products absorbed by the hyaluronic acid together with fibrin in the excreted fluids adheres the dressing to the wound, forming an "artificial, reinforced scab" preventing propagation of any infection foci. As in General Example 1, the epithelialization progresses (usually on dermal remnants) as depicted in FIG. 3, and the keratinized epidermal layer detaches the wound dressing from the wound. The detached wound dressing areas can be sheared off by scissors. The adherent wound dressing allows early wound care in outpatient conditions. As long as this artificial scab exists the dressing maintains its original color and appearance. If a non-healing wound persists beyond hydration potential of the hyaluronic acid (usually in the case of a full thickness defect), a wet, darker discoloration appears area due to the excreted fluids. This can be used as a diagnostic marker for treatment change. In order to avoid granulation tissue formation corticosteroid solution or cream can applied on the surface of the wound dressing, seeping through to the wound surface. If the dressing dries and the area is small, the wound dressing may be kept in place until healing (epithelialization) is completed. If the dressing continues to change appearance, the discolored area can be excised to allow direct care (i.e. grafting) of the wound. As previously mentioned, in a long standing dressing (>one week) it is possible to add hyaluronic acid to the wound dressing by applying it on the external surface.

General Example 3

Treatment of a Wound Bed with Persistent, Heavily Contaminated Eschar

As described in General Examples 1 and 2, the serum and pus excreted at the wound surface advance along the conduit wall, are absorbed by the hyaluronic acid, hydrating it completely or partially (as depicted in FIG. 2), depending of the fluid quantity (moisture) at the wound surface. The nature of the pus changes and stain the wound dressing surface allowing accurate microorganism culture, diagnosis and treatment. The moistened hyaluronic acid prevents desiccation of the healing wound enhancing its epithelialization that is guided by the dressing surface. The moist environment together with the normal or increased inflammatory reaction promote the maceration of the eschar remnants ("autolysis") and usually resolution of the contaminated foci. The autolysis products absorbed by the hyaluronic acid together with fibrin in the excreted fluids adheres the dressing to the wound, forming an "artificial, reinforced scab" usually preventing propagation of infection. As in the previous example, the epithelialization progresses (usually on dermal remnants) the keratinized epidermal layer detaches the wound dressing from the wound. The detached wound dressing areas can be sheared off by scissors. The adherent wound dressing allows early wound care in outpatient conditions. As long as this artificial scab exists the dressing remains dry though color may be stained by the desiccated purulent excretions. If a non-healing wound or infection persist beyond hydration potential of the hyaluronic acid (usually in the case of a full thickness defect or contaminated eschar), a wet, darker discoloration or staining (according to the contaminant germ) area/s appear due to the excreted fluids. This can be used as a diagnostic marker for treatment change. In order to combat infection antiseptic or antibiotic solution or cream can applied on the surface of the wound dressing, seeping through to the wound surface. If the infection subsides the dressing dries, the wound dressing may be kept in place until healing (epithelialization) is completed. If the dressing continues to be purulent and moist and change appearance, antimicrobial solutions (e.g. mafenide acetate 5%) can be applied onto the dressings. In some cases vacuum can be applied to the external surface. In rare cases that the infection persists the discolored area can be excised to allow direct care (i.e. topical medication, drainage, excision or scraping) of the wound. In a long standing dressing (>a week) it is possible to add hyaluronic acid to the wound dressing by applying it on the external surface.

The good adherence while avoiding tissue in-growth, possibility of diagnosis and modulation of wound care by changing active medicaments through the dressing usually without disruption is unique and beneficial.

Experimental Example 1

Production of a Polyurethane Foam Containing Hyaluronic Acid

Open conduit polyurethane foam was treated with a solution of sodium hyaluronate to provide a polyurethane foam dressing having about 0.005 grams of dry sodium hyaluronate per $cm^3$ of foam. A flat sheet (0.4×20×20 cm) of polyurethane foam (300 conduits per $cm^2$ surface area, conduit diameter about 500 µm; obtained from Ashkelon Polymers Industries Ltd., Israel) was covered on its upper surface by application of 40 ml of sodium hyaluronate solution 2.1% (obtained from Bio-Technology General Ltd., Israel). The covered sheet was placed on a 20×20 cm permeable screen-wall of a vacuum box, and a burst of low vacuum (−20 mmHg) was applied for 5 minutes. As soon as solution was no longer visible at the surface of the foam, the sheet was placed into a vacuum desiccation box and kept under a constant vacuum (−550 mmHg) for 48 hour at 26 C.°. The treated sheet of foam was stored in a dry environment until use Experimental Example 2

Treatment of a Deep Second Degree Burn

Figure 4D:
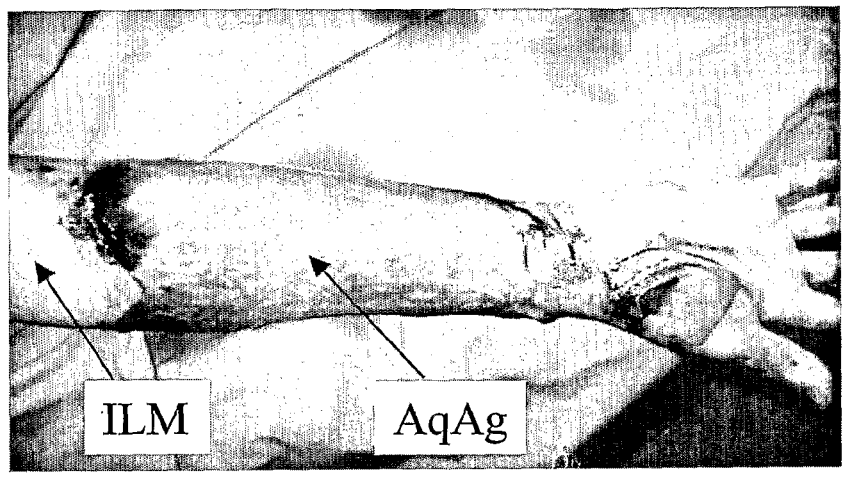
FIG. 4d shows that at Day 7 post dressing the ILM maintains its integrity, while AqAg shows tearing and tissue ingrowth.
Figure 4E:
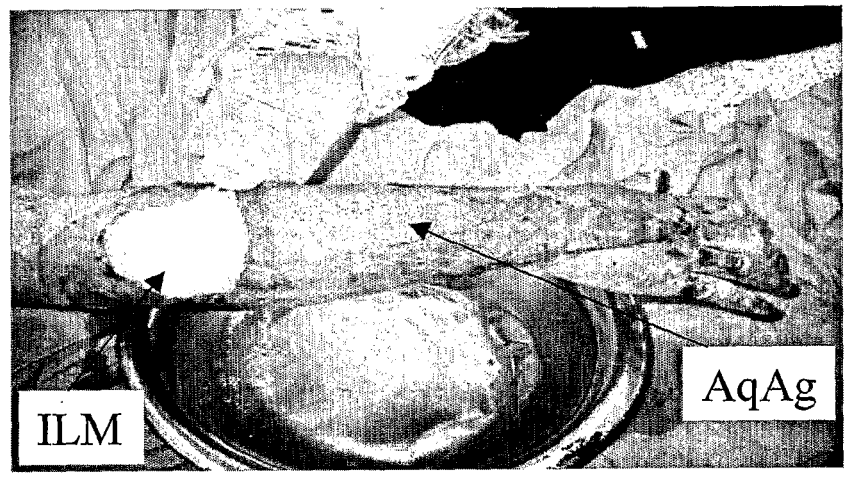
FIG. 4e shows application of corticosteroid solution at Day 9 post dressing.
Figure 4F:
FIG. 4f shows that at Day 13 post dressing the ILM yields easily to peeling, while AqAg remains adherent to the wound bed.

An adult male patient having sustained a deep second degree scald burn along the right forearm (elbow to palm) was treated in an out-patient dermatology clinical setting by rapid enzymatic debridement using Debrase® followed by wound dressing. Adjacent areas of the enzymatically debrided wound were dressed with either an open cell polyurethane foam (4 mm thickness; cell diameter about 500 µm; 300 cells/$cm^2$) prepared as in Experimental Example 1 so as to be coated on the exposed surfaces with dry hyaluronic acid (ILM), or the commercially available product Aquacel® $A_g$ ($A_qA_g$). FIG. 4 documents the healing process over approximately 2 weeks. FIG. 4a shows the burn wound following rapid enzymatic debridement with Debrase®. FIG. 4b shows the burn wound at day 3 following dressing with the ILM dressing and the AqAg dressing at the two different sites. The ILM dressing site exhibits a very clear appearance with the wound dressing preserving its consistency and color due to absorption by an external gauze dressing of excreted fluids, while the AqAg site is relatively stained and imbibed by the wound exudates. FIG. 4c shows a close-up view of the burn wound at day 5 post dressing. The upper area of the photo shows the clean edge of the ILM, while the leather-like desiccated AqAg is seen to the right. In the center a bleeding bed where the AqAg moved and tore the healing bed surface is apparent. FIG. 4d shows the burn wound at day 7 post dressing. The ILM dressing has preserved its integrity, while the AqAg dressing has undergone accidental tearing and tissue in-growth. FIG. 4e shows the burn wound at day 9 post dressing, showing progression of epithelialization. The ILM dressing over the healed portion of the wound is cut and removed, and corticosteroid solution is applied to control granulation tissue and epithelialization. In contrast, the AqAg site shows a stained, dry surface that has not transferred any medication through to the healing bed. FIG. 4f shows the burn wound at day 13 post dressing showing completion of healing at the site of the ILM dressing. The ILM dressing is easily peeled off the epitheiialized wound while the AqAg dressing adheres tightly to the bed.

Experimental Example 3

Treatment of an Inflicted Burn Wound

FIG. 5 shows a sequence of photographs documenting treatment of an inflicted burn wound in an experiment piglet system (20-25 kg animal). Standard deep burns (4.5 cm×4.5 cm) were inflicted, in which the center of each burn is full thickness and the remainder is a deep dermal, second degree burn.

FIG. 5a shows the appearance of the burn wound at day 1, immediately following burn infliction. FIG. 5b shows the appearance of the burn wound at day 1, following rapid enzymatic debridement with a commercial preparation of bromelain-derived enzymes, carried out four hours following burn infliction. The enzymatically debrided wound was then dressed with an open-cell polyurethane foam-hyaluronic acid dressing prepared as described in Experimental Example 1. FIG. 5c shows the wound at day 4, exhibiting discoloration typical of full thickness defects. The non-adherent edges of the dressing are cut away. FIG. 5d shows the wound at day 7, following soaking the dressing with Sulfamylon©. FIG. 5e shows the wound at day 9, exhibiting a clear and clean appearance, and significantly improved over its appearance in FIG. 5d. FIGS. 5f and 5g show the wound at day 12. Healing is progressing slowly, the free edges of the dressing are excised away (FIG. 5f), and hyaluronic acid cream is applied over the dressing (FIG. 5g). FIG. 5h shows the progression of wound healing at day 15. The dressing over the healed wound is excised away leaving a small adherent island over the healing full thickness wound. FIG. 5i shows the wound at day 17. The dressing has been peeled off the healing wound, showing that the central full thickness wound is not healed as yet, presenting a flat clean bed. FIG. 5j shows the wound at day 22, showing complete epithelialization.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A wound dressing, in the form of a dry flat sheet of synthetic polymer foam matrix having two opposed external surfaces, a first external surface configured to face the wound bed and a second external surface exposed to the external environment, the matrix comprising an open conduit polymer foam and at least one gel-forming hydrophilic polysaccharide, wherein the polysaccharide is disposed in dry form on the inner surfaces of the open conduits within the foam.

2. The wound dressing according to claim 1, wherein the open conduit polymer foam comprises a material selected from the group consisting of: a polyurethane, a cellulose derivative, a polyolefin, a polyvinylchloride, a polyvinylfluoride, a poly(vinylimidazole), a polyacrylate, a ethylene-vinyl acetate copolymer, a polystyrene, and a polyethylene oxide.

3. The wound dressing according to claim 1, wherein the open conduit polymer foam comprises open conduit polyurethane.

4. The wound dressing according to claim 3, wherein the polyurethane is selected from the group consisting of: a polyester polyurethane, a polyether polyurethane and a cross-linked polyurethane.

5. The wound dressing according to claim 1, wherein the open conduit polymer foam is substantially non-biodegradable.

6. The wound dressing according to claim 1, wherein the gel-forming hydrophilic polysaccharide is selected from the group consisting of: hyaluronic acid; a sulfated glycosaminoglycan; chitosan; alginate; hydroxyethyl cellulose; carboxymethyl cellulose; a cellulose derivative; pectin; gum arabic; and pharmaceutically acceptable salts and derivatives thereof and combinations thereof.

7. The wound dressing according to claim 6, wherein the gel-forming hydrophilic polysaccharide is hyaluronic acid or a pharmaceutically acceptable salt or derivative thereof.

8. The wound dressing according to claim 1, wherein the polysaccharide is further disposed in dry form on at least one of the opposing external surfaces of the foam.

9. The wound dressing of claim 1, wherein the thickness of the dry sheet of foam is from about 2 to about 12 mm, prior to hydration.

10. The wound dressing according to claim 1, wherein the hydrophilic polysaccharide is present in an amount of from about 0.001 gram to about 1.0 gram per $cm^3$ of polymer foam.

11. The wound dressing according to claim 1, wherein the open conduit polymer foam comprises open conduit polyurethane, and wherein the gel-forming hydrophilic polysaccharide is hyaluronic acid or a pharmaceutically acceptable salt or derivative thereof.

12. The wound dressing according to claim 11, wherein the hyaluronic acid is present in an amount of from about 0.001 gram to about 0.01 gram per $cm^3$ of polyurethane foam.

13. The wound dressing according to claim 1, wherein the diameter of the conduits within the polymer foam is between about 300 μm and about 5000 μm.

14. The wound dressing according to claim 1, wherein at least 75% of the conduits within the polymer foam are substantially continuous between the opposing outer surfaces of the foam.

15. The wound dressing according to claim 1, wherein the polymer foam has from about 200 to about 500 conduit openings per $cm^2$.

16. The wound dressing according to claim 1, wherein the polymer foam has a density from about 0.1 to about 0.4 $g/cm^3$.

17. The wound dressing according to claim 1, further comprising a pharmaceutical ingredient selected from the group consisting of: a corticosteroid, a growth factor, a bacteriocide, bacteriostatic, an antibiotic, an additional polysaccharide and a plant extract.

18. The wound dressing according to claim 1, wherein the polymer foam matrix comprises open conduit polyurethane foam, wherein the diameter of the conduits within the polyurethane foam is between about 300 μm and about 1000 μm, and wherein said at least one polysaccharide comprises hyaluronic acid or a pharmaceutically acceptable salt or derivative thereof, present in an amount from about 0.001 gram to about 0.01 gram per $cm^3$ of polyurethane foam.

19. A method for promoting healing of a debrided wound bed in a subject in need thereof, the method comprising the step of applying over the wound bed a wound dressing according to claim 1, thereby promoting healing of the debrided wound bed in the subject.

20. The method according to claim 19, wherein the method is carried out on an enzymatically debrided wound bed following an enzymatic debridement procedure, wherein the enzymatic debridement procedure comprises application of an enzyme selected from the group consisting of: bromelain derivatives, debridase, collagenase, papain derivatives, streptokinase, sutilains, fibrinolysin, deoxyribonuclease, krill derivatives, trypsin and combinations thereof.

21. The method according to claim 19, wherein the wound bed is originated from a venous leg ulcer, a pressure ulcer, a diabetic foot ulcer, a burn, an amputation wound, a split-skin graft, a skin graft donor site, a traumatic wound, a bite wound, a frostbite wound, a dermabrasion, or a surgical wound.

22. The method according to claim 19, further comprising the step of applying a pharmaceutical agent to the external surface of the foam which does not face the wound bed, wherein the pharmaceutical agent is selected from the group consisting of: a corticosteroid, a growth factor, a bacteriocide, bacteriostatic, an antibiotic, an additional polysaccharide and a plant extract.

23. A method for treating an enzymatically debrided wound bed in a subject in need thereof, the method comprising the step of applying over the wound bed a wound dressing, wherein the wound dressing comprises an open conduit polyurethane foam and hyaluronic acid or a pharmaceutically acceptable salt or derivative thereof, wherein the diameter of the conduits within the polyurethane foam is between about 300 μm and about 5000 μm, and wherein the hyaluronic acid is disposed in dry form on the inner surfaces of the conduits within the polyurethane foam, thereby treating the enzymatically debrided wound bed in the subject.

24. A method for producing the wound dressing according to claim 1, the method comprising the steps: (i) applying hyaluronic acid in the form of a solution to at least one external surface of the polyurethane foam so as to cover said external surface; and (ii) subjecting the foam obtained in (i) to drying under vacuum.

25. The method of claim 24, wherein the amount of hyaluronic acid applied to the external surface of the polyurethane foam in (i) is from about 1.0 to about 10.0 mg per $cm^2$ of said external surface of the polyurethane foam.

* * * * *